(12) United States Patent
Kusakabe et al.

(10) Patent No.: US 8,192,359 B2
(45) Date of Patent: Jun. 5, 2012

(54) FUNCTIONAL MODULE TYPE MEDICAL APPARATUS, FUNCTIONAL MODULE USED FOR THE APPARATUS, MEDICAL SYSTEM USING THE FUNCTIONAL MODULE AND MEDICAL FUNCTIONAL MODULE UNIT FOR USE IN MEDICAL TREATMENT AND/OR DIAGNOSIS

(75) Inventors: Hiroaki Kusakabe, Kyoto (JP); Naoki Katsuda, Kyoto (JP); Seiichiro Yamashita, Kyoto (JP); Kazunari Matoba, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 1035 days.

(21) Appl. No.: 10/145,268

(22) Filed: May 14, 2002

(65) Prior Publication Data

US 2002/0188183 A1 Dec. 12, 2002

(30) Foreign Application Priority Data

May 18, 2001 (JP) ................................ 2001-150189

(51) Int. Cl.
*A61B 17/24* (2006.01)
*A61C 1/00* (2006.01)
(52) U.S. Cl. ............. 600/300; 600/301; 433/27; 433/28
(58) Field of Classification Search .................. 600/300, 600/301; 128/903–905, 920; 433/27, 28
See application file for complete search history.

(56) References Cited

U.S. PATENT DOCUMENTS

| | | | | |
|---|---|---|---|---|
| 5,457,784 A | * | 10/1995 | Wells et al. ........................ 710/9 |
| 5,902,105 A | * | 5/1999 | Uejima et al. .................. 433/27 |
| 5,947,729 A | | 9/1999 | Bell | |
| 6,607,387 B2 | * | 8/2003 | Mault ........................... 433/215 |
| 6,790,178 B1 | * | 9/2004 | Mault et al. .................... 600/300 |

FOREIGN PATENT DOCUMENTS

| | | |
|---|---|---|
| DE | 154 11 97 | 8/1969 |
| DE | 423 24 87 | 4/1993 |
| DE | 195 20 765 | 12/1995 |
| DE | 195 08 481 | 9/1996 |
| DE | 197 55 169 | 6/1998 |
| EP | 0 329 944 | 8/1989 |
| JP | H7-51293 | 2/1995 |
| JP | H08-000640 | 1/1996 |
| JP | H8-19557 | 1/1996 |
| JP | H9-123924 | 5/1997 |
| JP | H9-248311 | 9/1997 |

(Continued)

*Primary Examiner* — Henry M Johnson, III
*Assistant Examiner* — Bobby Soriano
(74) *Attorney, Agent, or Firm* — DLA Piper LLP (US)

(57) ABSTRACT

A functional module type medical apparatus for use in medical treatment and/or diagnosis and a functional module with individual function of medical treatment and/or diagnosis are disclosed.

The functional module type medical apparatus comprises a common functional body with a module connection part, having at least one of a display section for displaying necessary information relating to medical treatment and/or diagnosis, an operation section for medical treatment and/or diagnosis, and a power source section for supplying driving power to the medical apparatus, in which the module connection part is constructed such that the corresponding connection part of a functional module having medical treatment and/or diagnosis is replaceably connected thereto, whereby the common functional body cooperatively functions in accordance with its individual function of the functional module when the functional module is connected thereto.

21 Claims, 17 Drawing Sheets

FOREIGN PATENT DOCUMENTS

| | | |
|---|---|---|
| JP | H10-127708 | 5/1998 |
| JP | H10-224260 | 8/1998 |
| JP | H11-244304 | 9/1999 |
| JP | 2000-113088 | 4/2000 |
| JP | 2000-254153 | 9/2000 |
| JP | 2000-288001 | 10/2000 |
| WO | WO 94/10931 | 5/1994 |
| WO | WO 96/13216 | 5/1996 |
| WO | WO 98/08453 | 3/1998 |

* cited by examiner

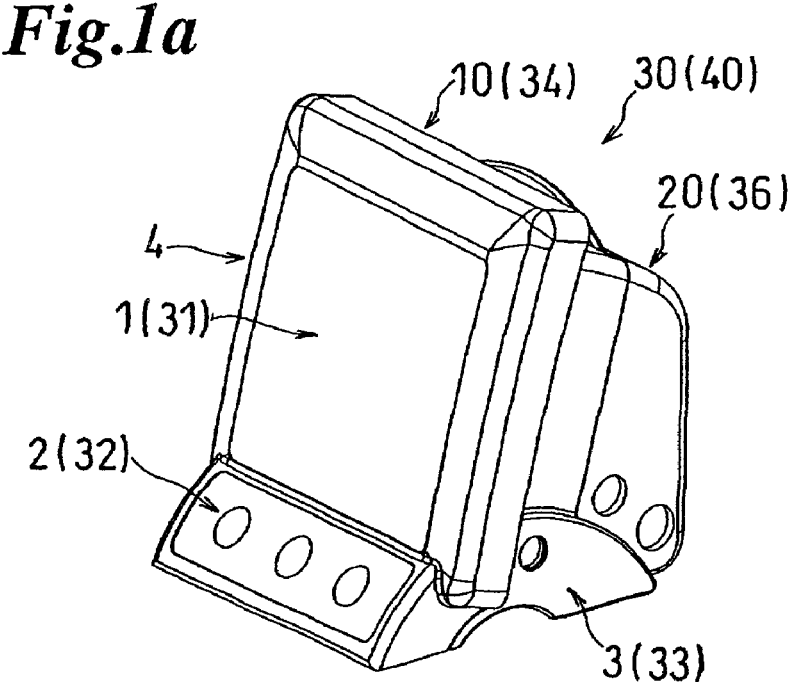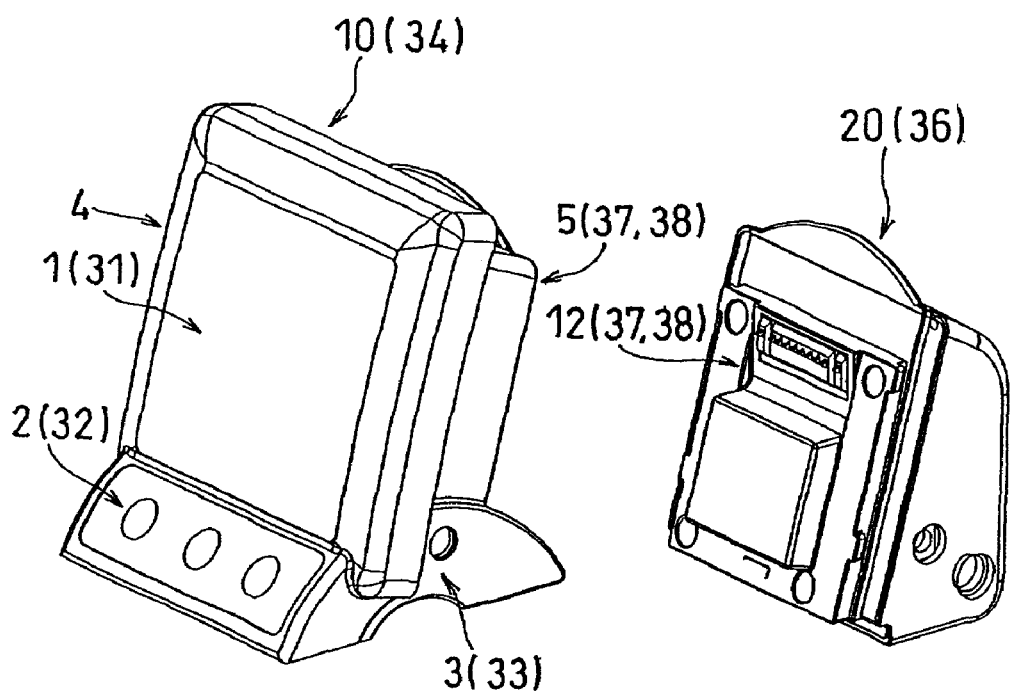

(a1) 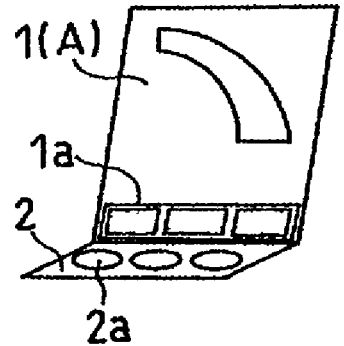 (a2) 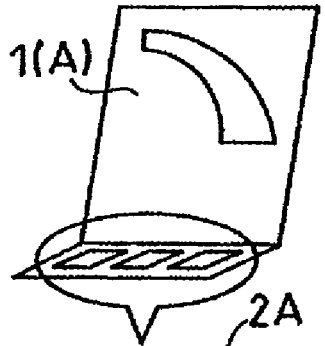 (a3) 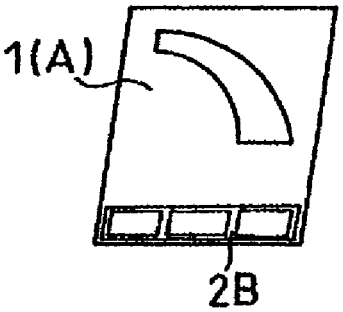
(b1) 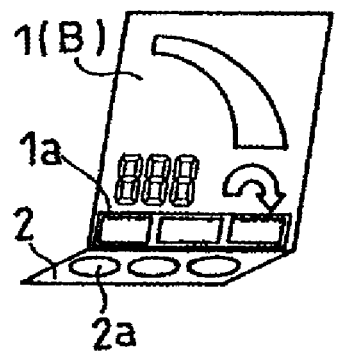 (b2) 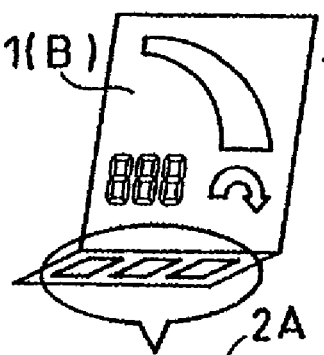 (b3) 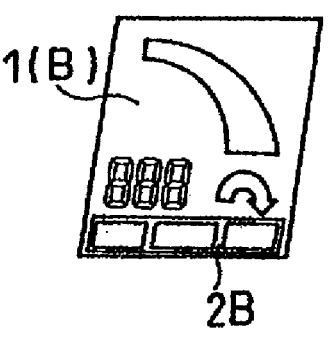
*Fig.3*

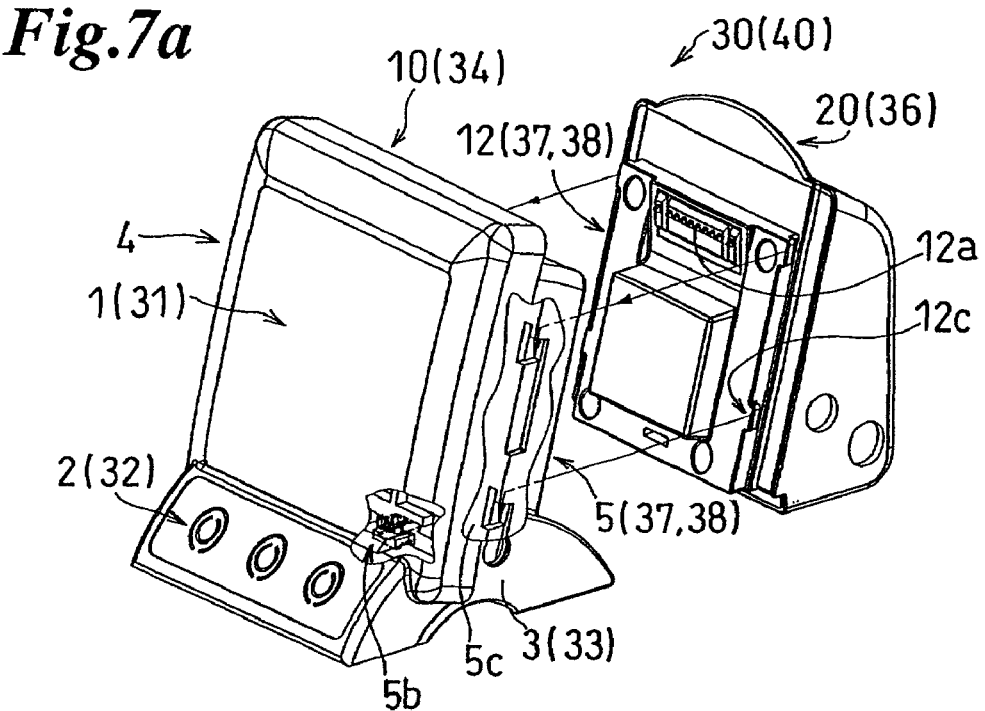
*Fig.7a*
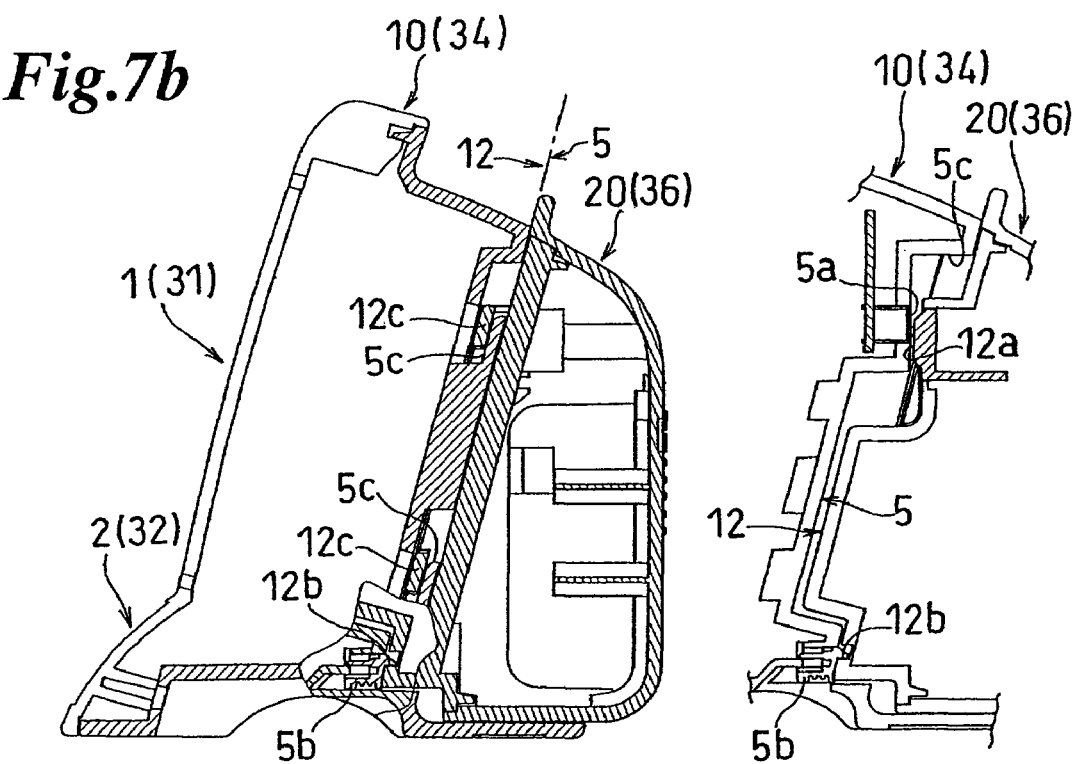
*Fig.7b*
*Fig.7c*

FUNCTIONAL MODULE TYPE MEDICAL APPARATUS, FUNCTIONAL MODULE USED FOR THE APPARATUS, MEDICAL SYSTEM USING THE FUNCTIONAL MODULE AND MEDICAL FUNCTIONAL MODULE UNIT FOR USE IN MEDICAL TREATMENT AND/OR DIAGNOSIS

FIELD OF THE INVENTION

The present invention relates to a functional module type medical apparatus, a functional module used for the apparatus, medical apparatus using such medical functional module, which are suitable for medical treatment or diagnosis for use in medical or dental fields.

PRIOR ART

In conventional medical or dental field, for example especially in the dental field, most of dental treatment and diagnosis is conducted by using a medical equipment having as standard specification a main treatment body for general treatment or diagnosis (referred hereinafter as a treatment or diagnosis unit).

However, as for such medical equipment, they are usually not provided with exclusive instrument, such as an ultrasonic scaler or a root canal length measurer, thus in case when they are required for use, such exclusive instrument is independently installed near such medical equipment and is used for conducting required specific treatment or diagnosis.

The above treatment or diagnosis units are usually made as a special medical equipment with exclusive treatment or diagnosis function, in which one function is incorporated into one body for effectively carrying out such medical function.

However, in such special medical equipments, various parts mentioned above are able to be essentially utilized in a manner of common use for other special medical equipment, thus such way as to incorporate such parts individually into the equipment nevertheless would make the equipment complicated and would fail to save space, and they would be rather wasteful.

On the other hand, in other medical equipment for use in treatment or diagnosis, for example, a multifunction apparatus has been proposed and used in which the apparatus has combined function of measuring root canal length as diagnosis function and of enlarging root canal for treatment, thus according to which dental operation for a root canal of a patient can be easily conducted while monitoring a tip position of a treatment file in the oral cavity of the patient.

Japanese patent application H11-244304 having been laid open discloses such multifunction type dental apparatus called as a micro-engine driven apparatus interlocked with a root canal length measuring apparatus, of which outside view is shown as FIG. 17.

This apparatus 100 comprises a root canal enlarger and a root canal length measurer, both are replaceably integrated and connected via a cable 105.

The root canal enlarger 110 comprises a display section for displaying the rotation status of a file F which enlarges a root canal, operation section for operation of rotation (a foot controller), and an instrument (a micro-motor handpiece) connected to the enlarger 110 via a connection code 107, in which the rotation of the file F which is fastened at the tip of the instrument 108 can be freely controlled by operating an operation section 102.

The root canal length measure 120 comprises a positive pole 116A electrically leading to the file F, an instrument 116 composed of negative pole 116B electrically leading to tooth as an object of root canal measuring, and a display section 118 for displaying measured data (an electrical resistance between oral mucous membrane and the file F inserted into the root canal) measured at the instrument 116.

According to the apparatus above mentioned, by integrating the root canal enlarger 110 with the root canal length measurer, a file F of root canal enlarger 110 can be driven while viewing the measured value of root canal measurer 120 so that root canal can be viewed by more larger size.

However, as for the apparatus 100 shown in FIG. 10, plural functions are interlocked or combined, although power source or the like is commonly used, such combinations of interlocking are limited to one to one combination irrespective of common use of its display section, thus more improvements have been required.

Further, in other conventional medical equipment, although there exists such medical equipment in which a plurality of function are interlocked or combined each other, for example, as for power source, it is so installed as to be commonly used, but such interlocking or combination with plurality of equipments each other is limited as a manner of one to one combination use, without consideration of common use even for display section.

Therefore more improvements for such medical equipment for medical treatment or diagnosis have been required.

Accordingly, it is a primary object of the present invention to solve such problems and to provide a compact functional module type medical apparatus capable of saving space and reducing the cost irrespective of its kind function of medical treatment and diagnosis, in case when a plurality of medical treatment and diagnosis is required.

It is a second object to provide a functional module with individual function of medical treatment and diagnosis used in combination with module type medical apparatus.

It is a third object to provide medical system using that functional module and a function module unit for medical treatment and diagnosis.

The above and other objects and features of the present invention will appear more fully hereinafter from a consideration of the following description taken in connection with the accompanying drawing wherein various embodiments are illustrated by way of preferred embodiments.

In this description on the present invention, the terms "for medical treatment and/or diagnosis" means not only for medical use but also for dental use. An apparatus for medical treatment and/or diagnosis includes any one in which electricity is used and, in addition to such one as to use water, or air. Also, in some cases, no electricity may be used at all.

The apparatus for medical treatment and/or diagnosis includes such medical apparatuses for cutting, grinding, spraying and emitting rinsing water and medical liquid water, such apparatus for treating using electricity or light, and such diagnosis apparatus for measuring voltage, current and the like by combination of specific electricity contact points.

In the dental field, such apparatuses involve various hand pieces, air turbine hand pieces, micro-motor hand pieces, scalers, photopolymerizer, semiconductor laser, root canal enlarger, root canal filler, caries detector, root canal length measurer, pulp diagnosis apparatus, oral camera and pocket measurer and the like.

The medical apparatuses for medical treatment or diagnosis involve all of apparatus used in medical treatment and diagnosis, i.e. medical unit, dental unit, treatment and diagnosis apparatus used in otorhinolargyology, obestetrics and gynecology, urology, ohthalmology, and the like.

The function type medical treatment and diagnosis of the present invention is characterized by a common functional body with a module connection part comprising at least a display section to display necessary information relating to medical treatment and/or diagnosis, an operation section for medical treatment and/or diagnosis, and a power source section for supplying driving power to the medical apparatus, in which the module connection part is so constructed as to replaceably connect various functional modules having individual medical function of medical treatment and/or diagnosis, whereby the common function body cooperatively functions in accordance with the functional module so as to carry out its function of medical treatment and/or diagnosis of the functional module to be connected.

In a preferred embodiment of the present invention, such functional module type medical apparatus comprises a common functional body with a module connection part, wherein the common functional body has at least one of a display section for displaying necessary information relating to medical treatment and/or diagnosis, an operation section for medical treatment and/or diagnosis, a power source for supplying driving power to the apparatus, whereas the module connection part of the functional module is constructed such that the corresponding connection part of the functional module is connected thereto, whereby the common functional body cooperatively functions in accordance with the practicable function of the functional module when the functional module is connected to the medical apparatus.

This medical apparatus may have individual medical treatment and/or diagnosis functions by itself, namely the apparatus has not only single function but also combined functions as the functional module has.

The functional module type medical apparatus for use in medical treatment and/or diagnosis of the present invention is also characterized by its module connection part.

The module connection part of the medical apparatus has as a basic structure an electrical connection part or a mechanical connection part, and in a preferred embodiment, the function module has an electrical and mechanical connection portion for making mechanical and electrical connection at the same time on connection each other, further the medical apparatus and the functional module are designed such that both are integrated as one unit structure when the corresponding module connection parts of both are connected each other. In addition, in other embodiment of the present invention, the module connection part of the medical apparatus is constructed such that the functional module is replaceably connected thereto.

The functional module type medical apparatus for use in medical treatment and/or diagnosis of the present invention is also provided with module recognition means for discriminating its function kind of functional module connected to the medical apparatus.

This module recognition means involves such means as to receive a module code registered in the connected functional module through communication and decodes to recognize it, such means as to recognize ID cord from an ID element, and such means as to detect and measure intrinsic impedance of the connected functional module, and such means as to mechanically and electrically detect the shape of the individual connector with a functional module.

In one type of the functional module type medical apparatuses according to the present invention, communication information is transmitted between the medical apparatus and the functional module, both are connected each other, after recognition of the functional module, wherein such communication information includes at least one of: necessary information to be displayed, relating to medical treatment and/or diagnosis; function setting information for an operation section; medical treatment and/or diagnosis data; such machinery or control information about an instrument to be connected thereto.

According to the medical apparatus, after when such communication information is received between the apparatus and a functional module, a display section, an operation section, and a power source provided in the common functional body are set to specific function mode corresponding to the function of the functional module and then medical treatment and/or diagnosis are conducted in accordance with the function of the functional module, namely the display section, the operation section, and the power source provided in the common functional body cooperatively functions in accordance with the function module.

The functions of medical treatment or diagnosis are conducted by executing control software prepared in advance, for this purpose, software may be employed such exclusive software as to be stored in advance in the functional module, or such common software as to be stored in advance in the medical apparatus. In case that common software are employed, such one as to be in advance forwarded to the medical apparatus by way of transmission.

The functional module type medical apparatus may be used by selectively connecting a functional module to its common functional body according to the purpose of medical treatment or diagnosis, and may be used by connecting plural functional modules, and in this case one of or all of practicable functions of the functional module may be carried out selectively or in parallel.

Also, the medical apparatus, in other preferred embodiment, has individual function of medical treatment and/or diagnosis by itself and a multi-joint connection part, whereby various multi-joint type instruments corresponding to the function of medical treatment and/or diagnosis can be replaceably connected to the medical apparatus.

Moreover, in other embodiment, the medical apparatus is characterized in that a battery as a driving power source for a common functional body is provided.

A functional module with individual function of medical treatment and/or diagnosis used for in combination with the medical apparatus is also proposed, in which such functional module has a corresponding module connection part.

The functional module proposed here as the present invention is characterized as follows.

Namely, the present functional module comprises a module connection part constructed as to be replaceably connected to the corresponding module connection part of a medical apparatus, and a recognition apply means for enabling the medical apparatus to discriminate its kind function of the functional module.

Its module connection part has as a basic structure an electrical connection part or a mechanical connection part, and in a preferred embodiment, the module connection part has an electrical and mechanical connection portion for making mechanical and electrical connection at the same time on connection to a medical apparatus each other, the functional module and a medical apparatus are designed such that both are integrated as one unit structure when the corresponding module connection parts of both are connected each other.

In addition, in other embodiment of the functional module, such functional module is made under the same standard for easy replaceable connection to a medical apparatus.

Moreover, such functional module with a multi-joint connection part, to which various multi-joint type instruments can be replaceably connected, is also proposed, in its preferred embodiment, the functional module has a sub-module connection part to which various functional modules are replaceably connected.

Moreover, such functional module having therein a battery serving a driving source to carry out medical treatment and/or diagnosis function, such functional module operating a common functional body in accordance with individual function of medical treatment and/or diagnosis by transmitting necessary information between the common functional body connected thereto, and such functional module storing in advance therein control software for realizing medical treatment and/or diagnosis are also proposed as the present invention.

A medical system is also proposed as the present invention, wherein the system comprises a treatment bed for holding a patient in sitting position or lying in face up position, a common functional body having a display section for displaying necessary information relating to medical treatment and/or diagnosis, and an operation section for medical treatment and/or diagnosis, and a module connection part to which a functional module with individual function of medical treatment and/or diagnosis is replaceably connected, whereby the common functional body cooperatively functions in accordance with the function of the functional module to be connected thereto, when the common functional body is connected to the functional module.

In addition, a functional module unit for use in medical treatment and/or diagnosis is further proposed, wherein the module unit comprises plural kinds of individual functional module units incorporating therein an operational control part corresponding to its individual function of medical treatment or diagnosis function, and a common functional module unit having at least a display section for displaying necessary information relating to medical treatment and/or diagnosis, and an operation section for medical treatment and/or diagnosis, the individual functional module unit being replaceably connected to the common functional module unit, wherein electrical connection portion and mechanical connection portion are correspondingly provided with the common functional module unit each other for integrating the individual functional module unit, and wherein the display section and the operation section of the common functional unit serves as that of the individual function module unit in accordance with the function module unit by changing its operation mode to such mode corresponding to the individual functional module when the individual functional module unit is connected to the common functional module unit, the common functional module unit discriminating the individual functional unit through the mutual communication with the individual functional module unit.

BRIEF DESCRIPTION OF THE DRAWINGS

FIG. 1 is one embodiment of a functional module type medical treatment apparatus and a functional module according to the present invention, wherein FIG. 1*a* is an external perspective view when both of them are combined, FIG. 1*b* is an external perspective view of the medical treatment and/or diagnosis apparatus, and FIG. 1*c* is an external perspective view of the functional module.

FIG. 2 is a display section according to the present invention, wherein

FIG. 3 shows several types of operation section corresponding to the display section of the present invention, wherein FIG. 3*a*1 FIG. 3*a*2 and FIG. 3*a*3 are a button type, a button type with a display, a display integrated type respectively, when the display shows such status that a root canal length is measured, while FIG. 3*b*1, FIG. 3*b*2 and FIG. 3*b*3 show corresponding view with respect to the same operation section when a root canal length is measured and a root canal is enlarged.

The enlarged view of the button 2*b* in FIG. 3*a*2 shows its contents and the contents are the same also in FIG. 3*a*1 and FIG. 3*a*3. Also the enlarged view of the button 2*b* in FIG. 3*b*2 shows its contents and the contents are the same also in FIG. 3*b*1 and FIG. 3*b*3.

Figure 4:
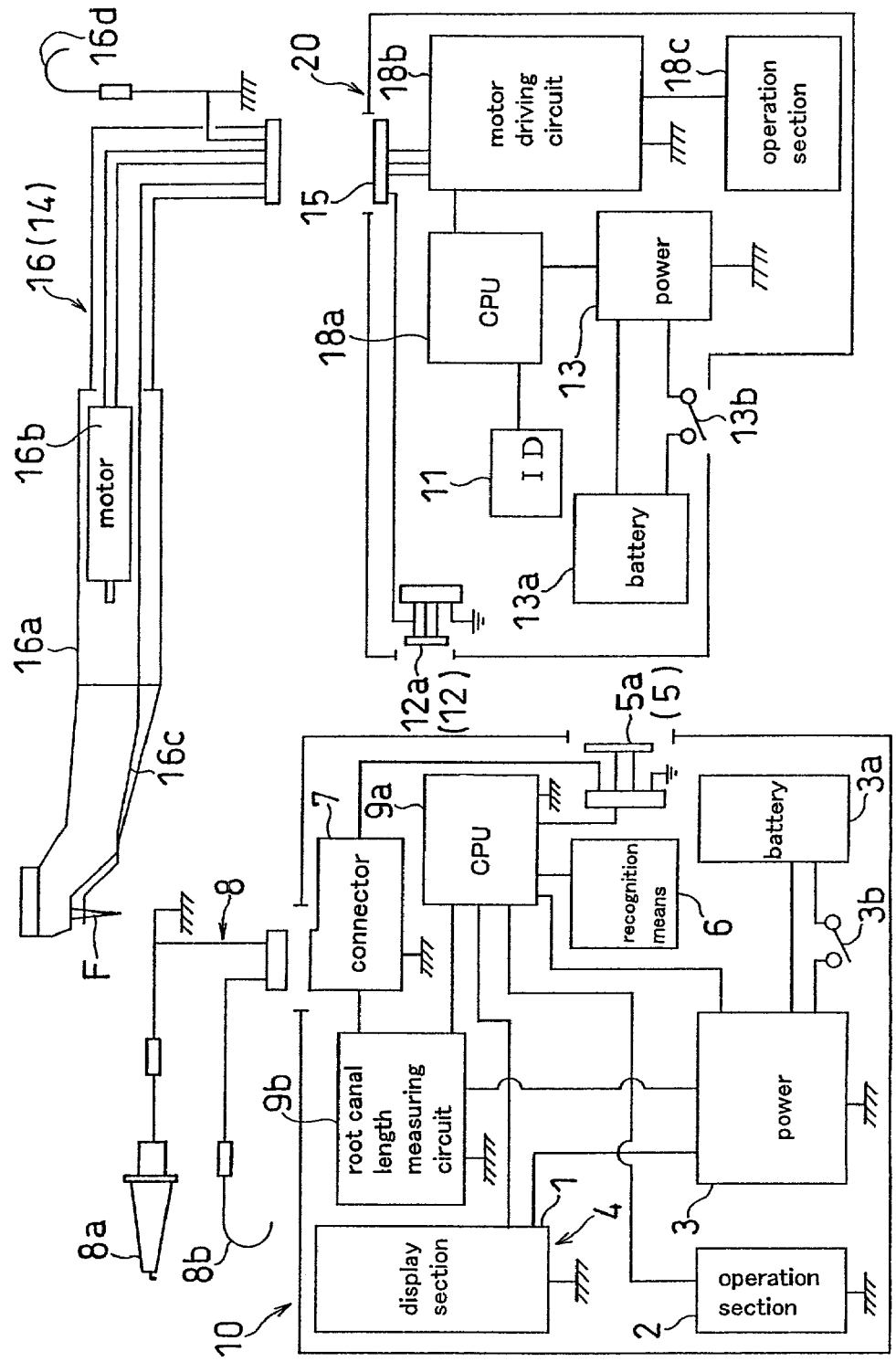

FIG. 4 is a block diagram showing one embodiment of a medical treatment and/or diagnosis apparatus and a functional module according to the present invention.

Figure 5A:
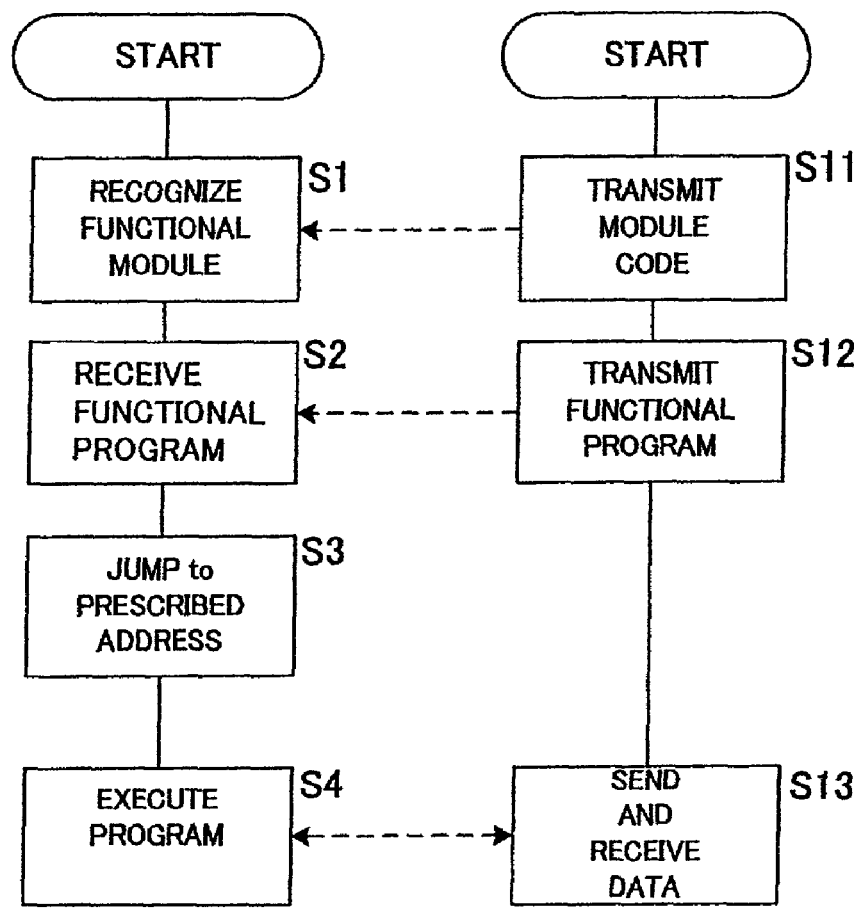
Figure 5B:
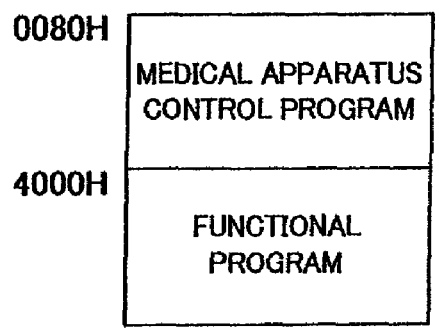

FIG. 5*a* is a flow chart explaining one embodiment of operational procedures of a medical treatment and/or diagnosis apparatus and a functional module according to the present invention and FIG. 5*b* shows a memory map of a medical treatment and/or diagnosis apparatus.

Figure 6:
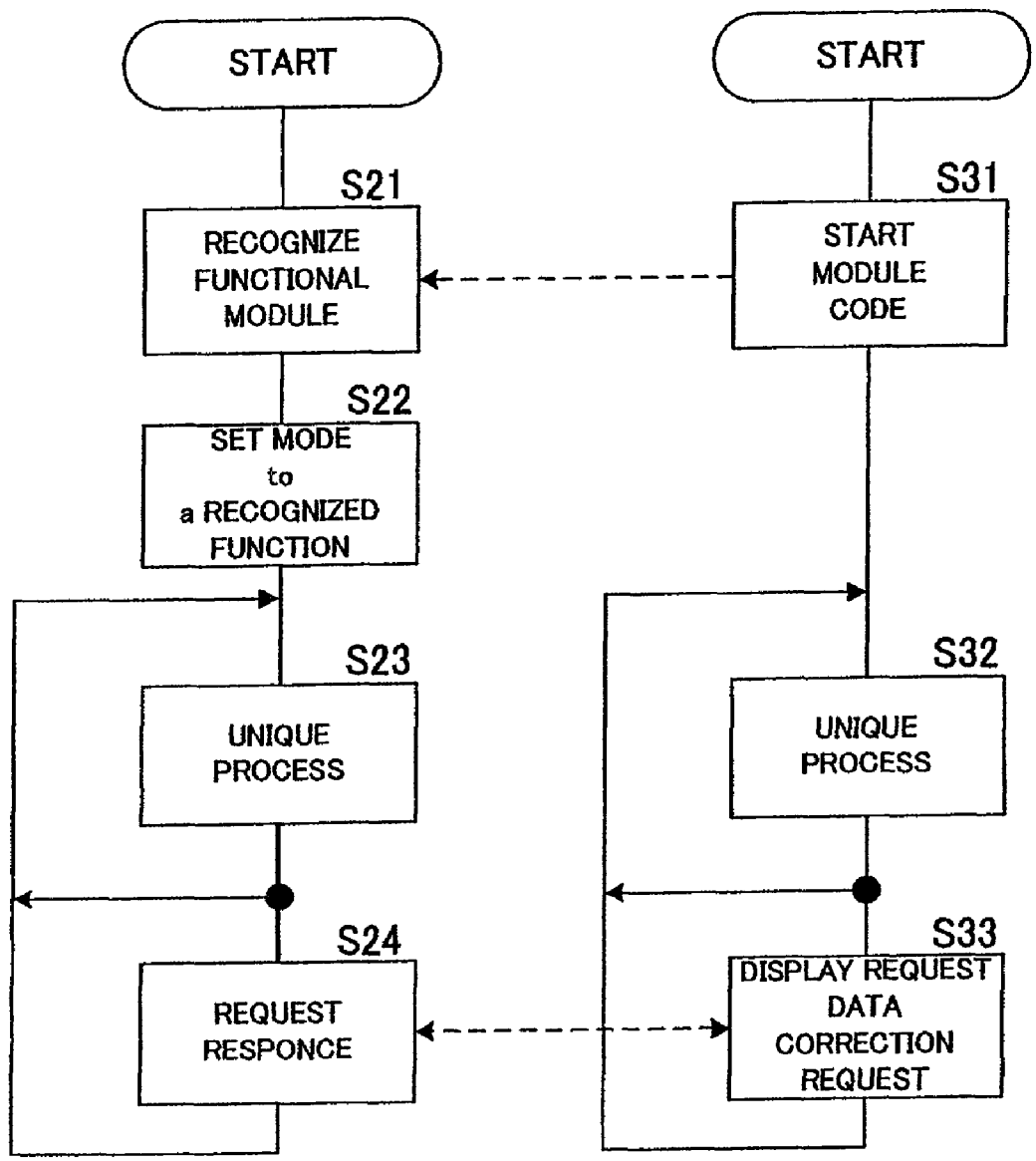

FIG. 6 is a flow chart explaining other embodiment of operational procedures of a medical treatment and/or diagnosis apparatus and a functional module according to the present invention.

FIG. 7 explains a connection between a medical treatment and/or diagnosis apparatus and a functional module according to the present invention, wherein FIG. 7*a* explains how to combine the apparatus with the module, FIG. 7*b* is a sectional view of a substantial part of the connection status, and FIG. 7*c* is a sectional view of a substantial part of an electrical connection.

Figure 8:
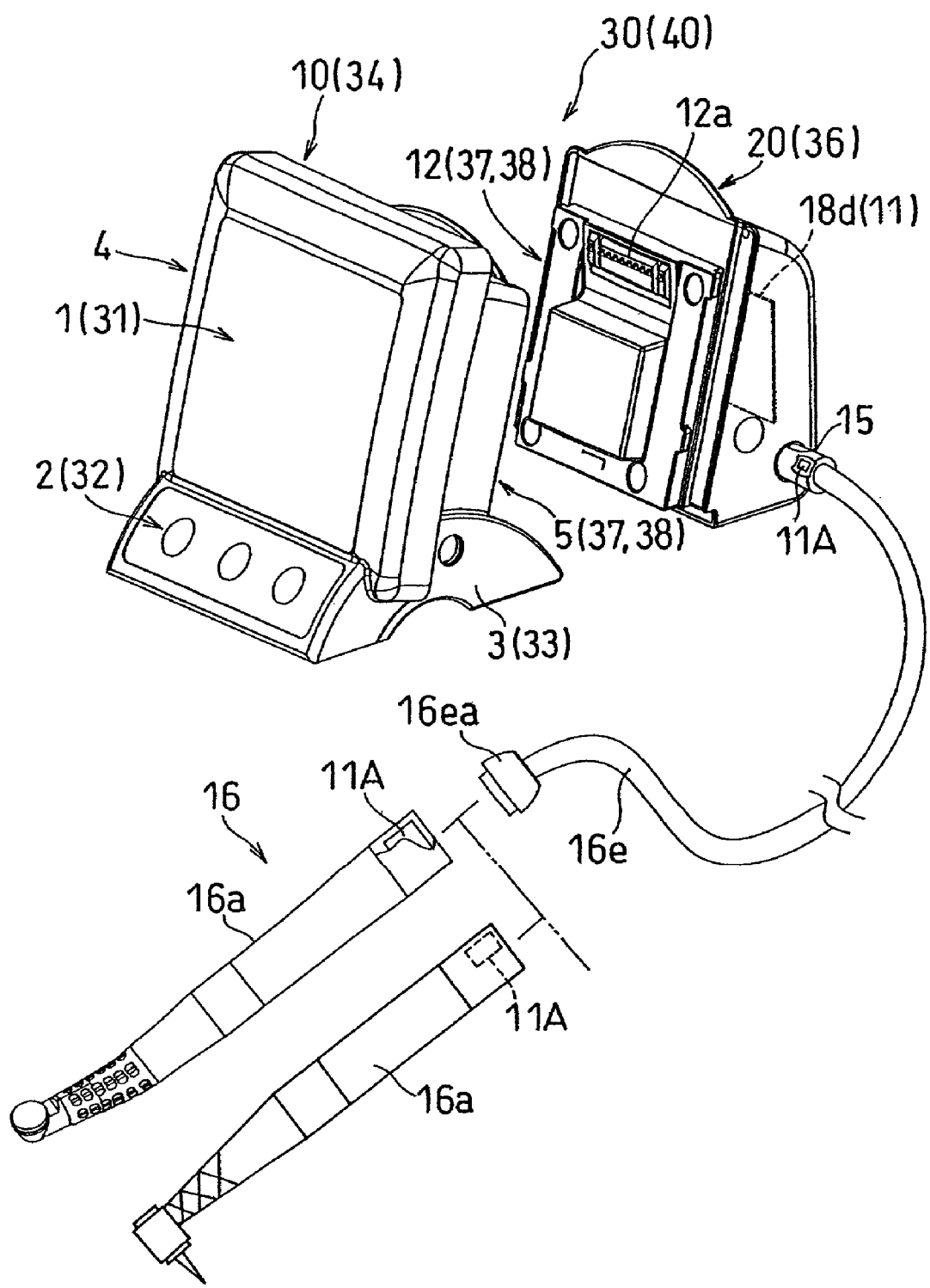

FIG. 8 is an external perspective view of a medical treatment and/or diagnosis apparatus, a functional module and a multi-joint type instrument, according to the present invention.

Figure 9A:
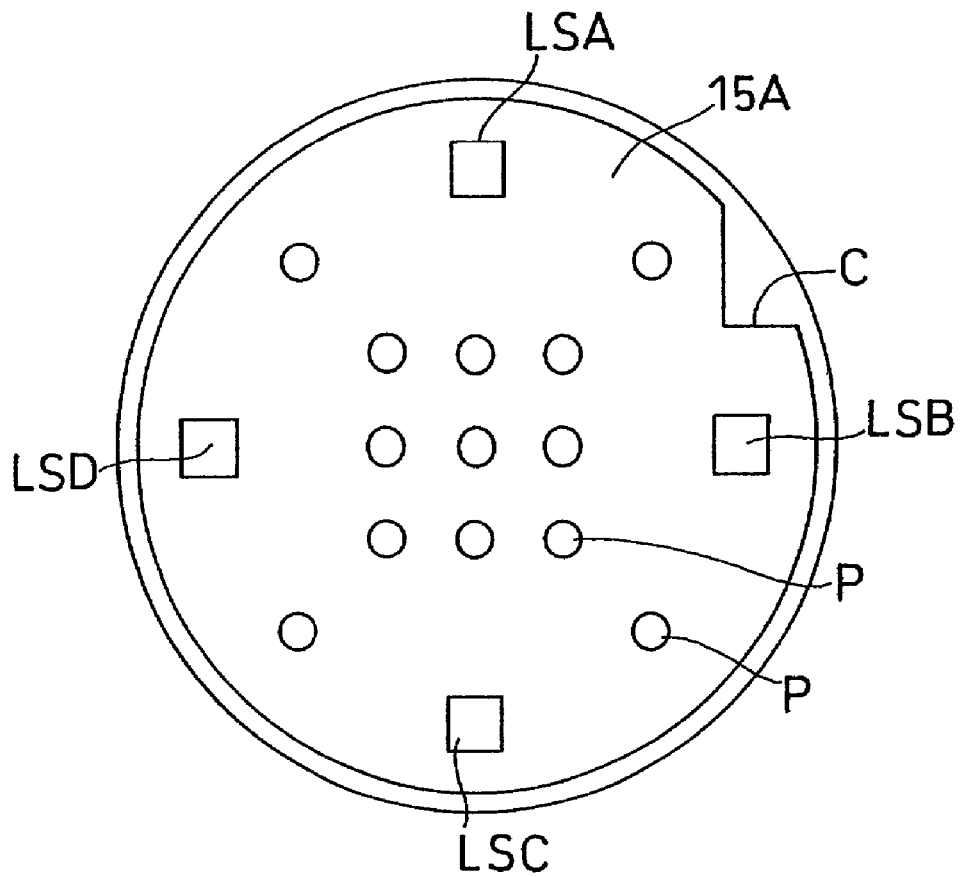
Figure 9B:
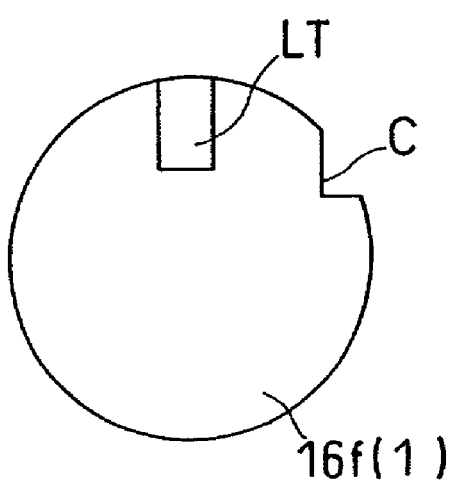
Figure 9C:
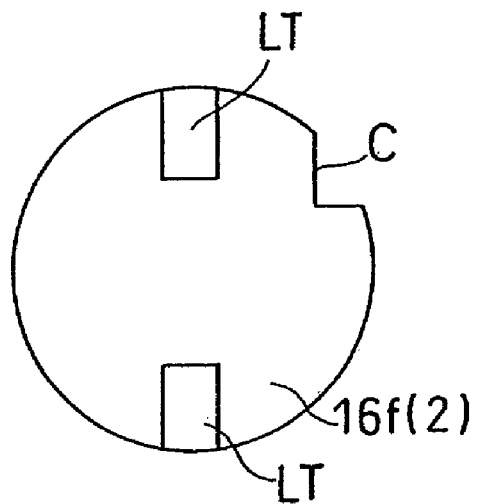

FIG. 9*a* is a conceptual view showing one embodiment of a connector constructing a module recognition means of a medical treatment and/or diagnosis apparatus according to the present invention, FIG. 9*b* shows a conceptual view of one embodiment of an individual connector of the functional module which is to be used in combination, and FIG. 9*c* is a conceptual view showing another embodiment of an individual connector.

Figure 10:
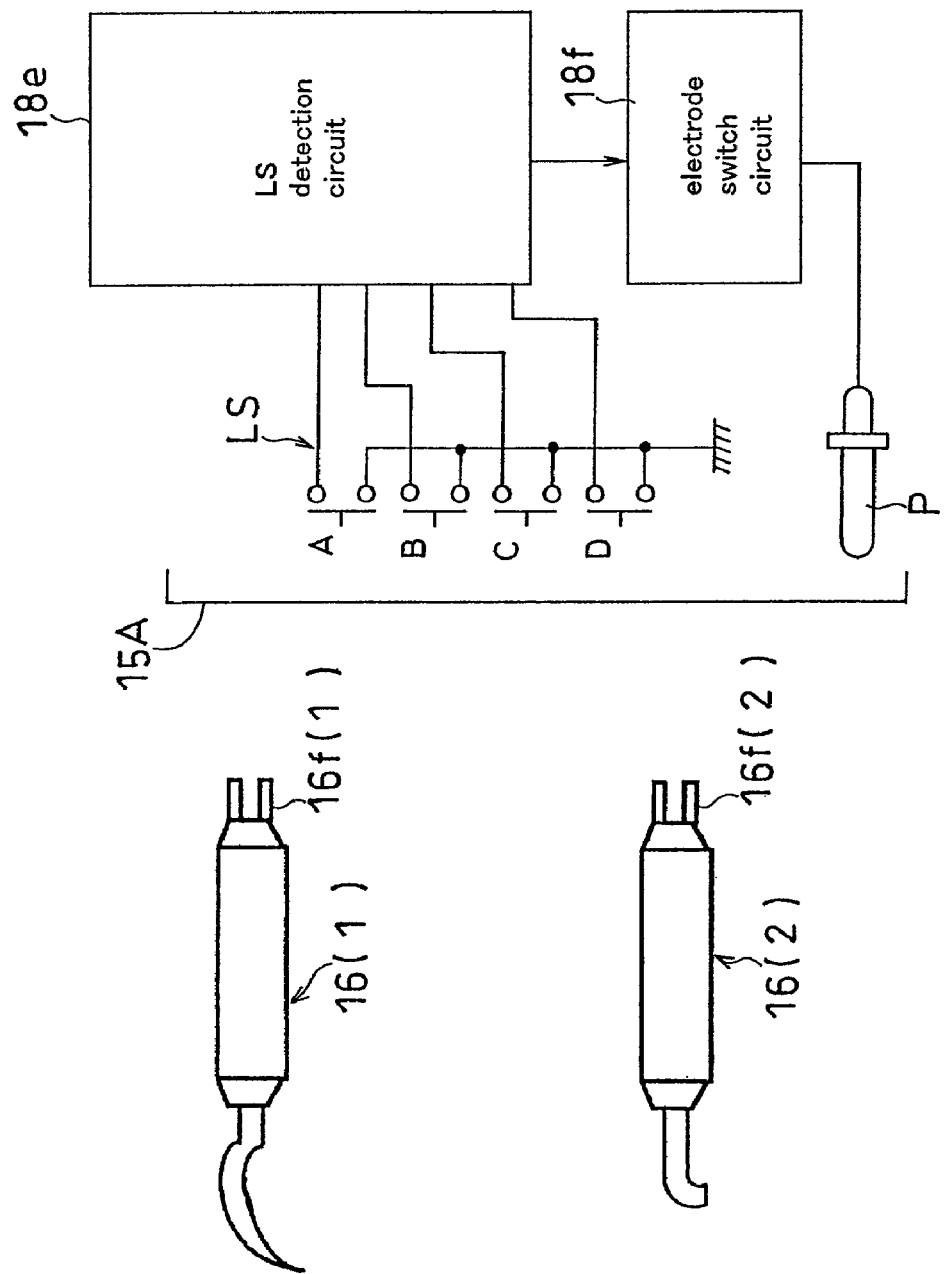

FIG. 10 explains a conceptual view showing one embodiment of a module recognition means provided in the present medical apparatus.

Figure 11:
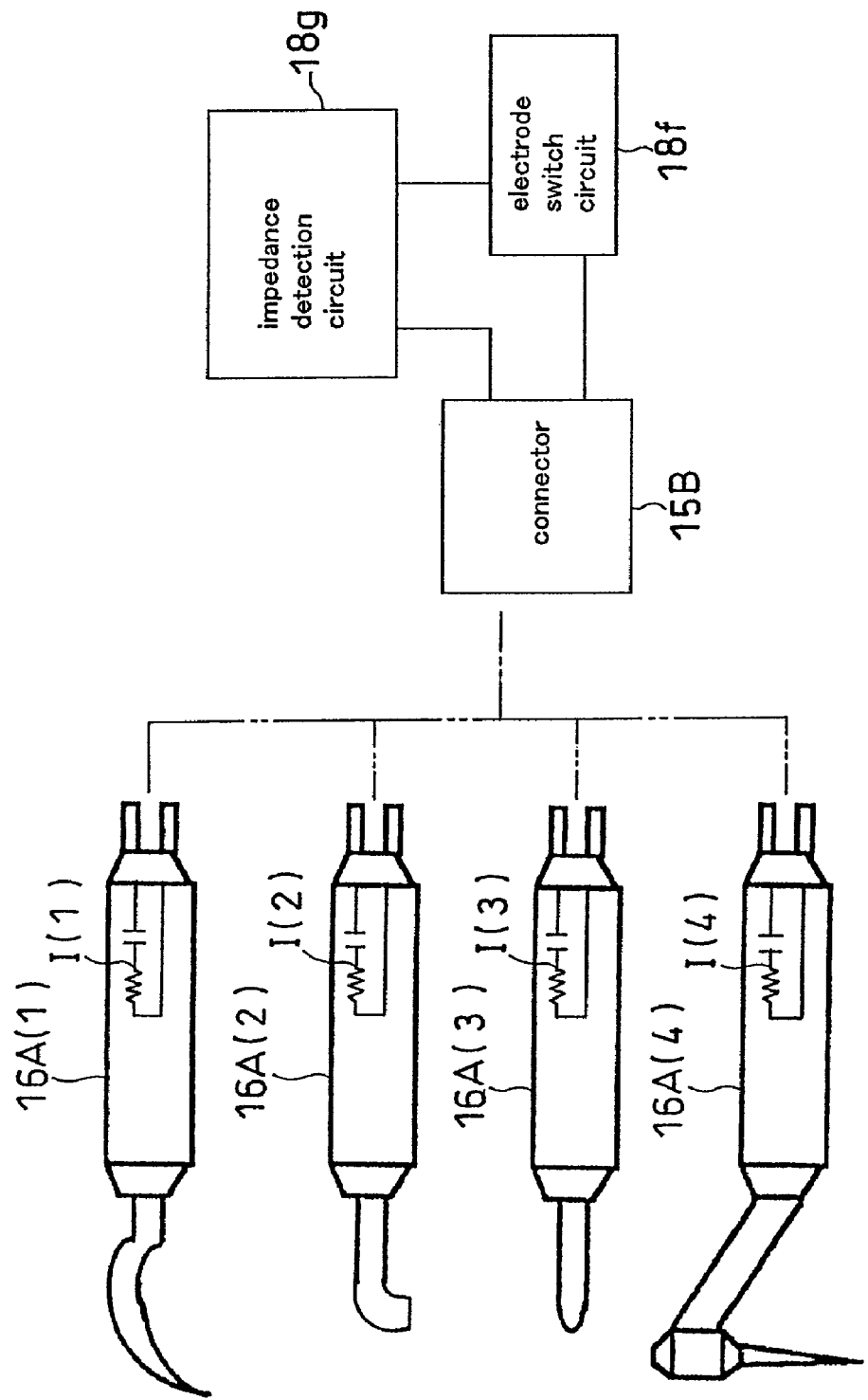

FIG. 11 is a conceptual view showing other embodiment of a module recognition means provided in the present medical apparatus.

Figure 12:
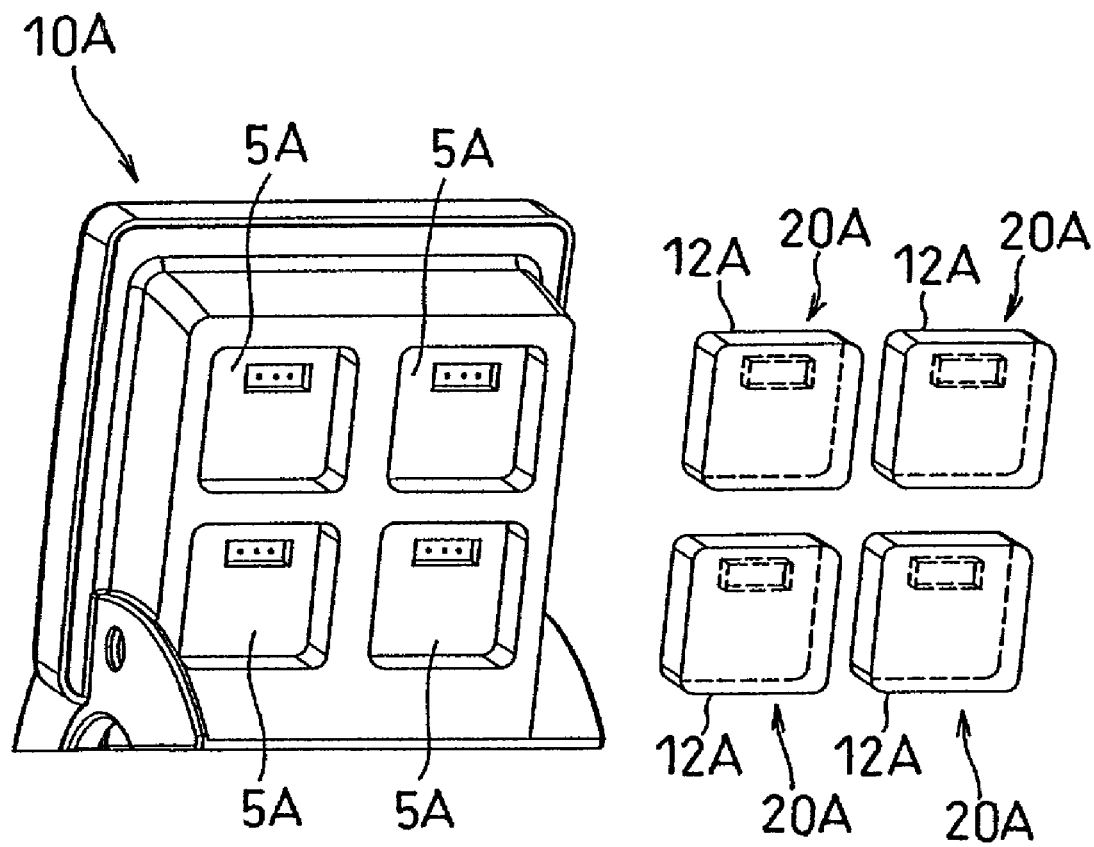

FIG. 12 is an external perspective view showing other embodiment of a module type medical treatment and/or diagnosis apparatus and a functional module according to the present invention.

Figure 13:
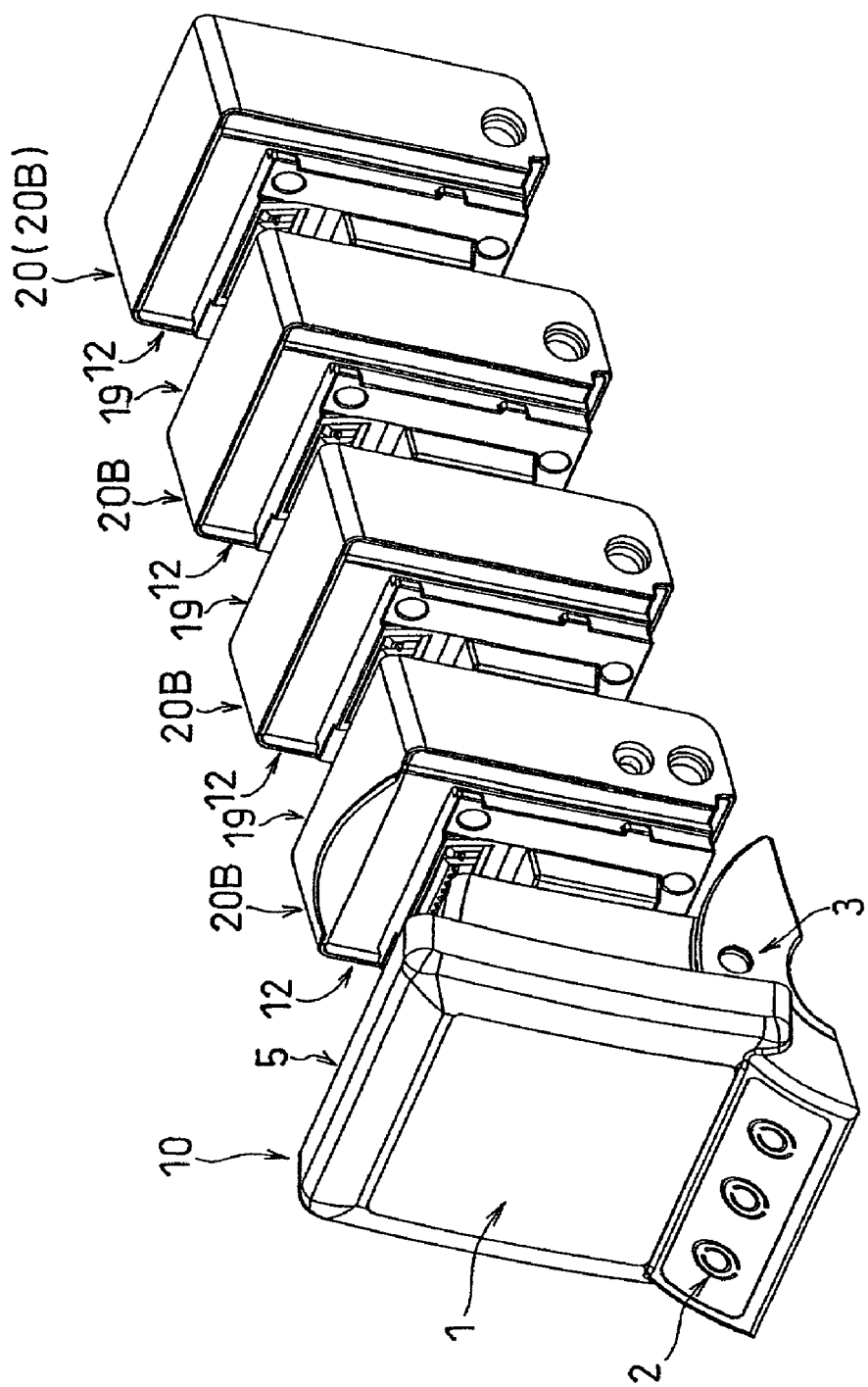

FIG. 13 is an external perspective view showing still other embodiment of a module type medical treatment and/or diagnosis apparatus and a functional module according to the present invention.

Figure 14A:
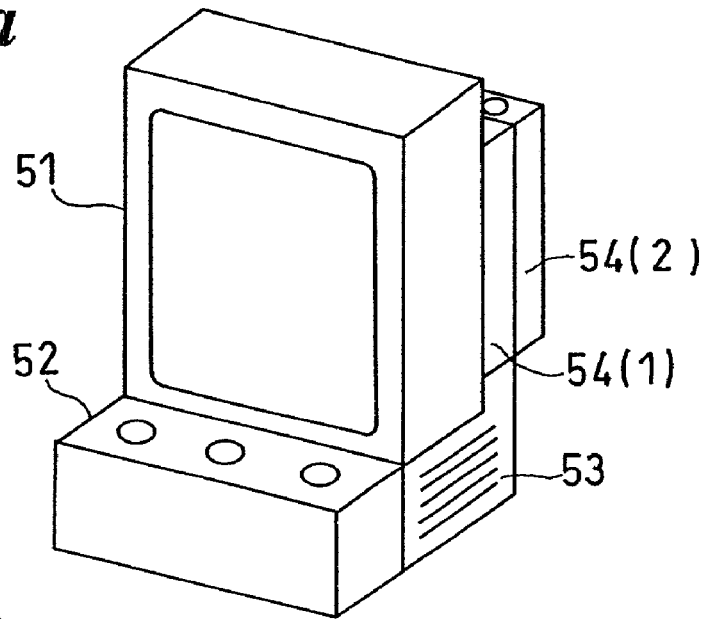
Figure 14B:
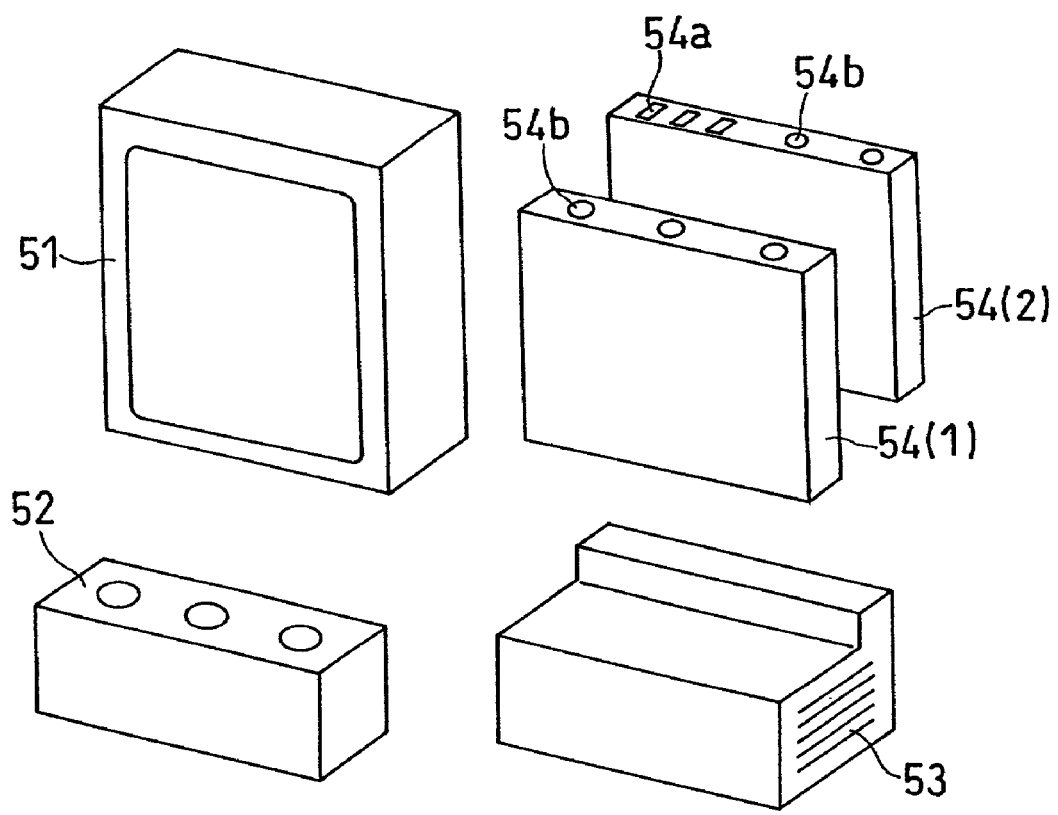

FIG. 14 is an external perspective view showing still other embodiment of combination with a module type medical treatment and/or diagnosis apparatus and a functional module according to the present invention, wherein FIG. 14*a* shows the entire structure of which all parts are combined, and FIG. 14*b* shows all parts each of which is separated.

Figure 15:
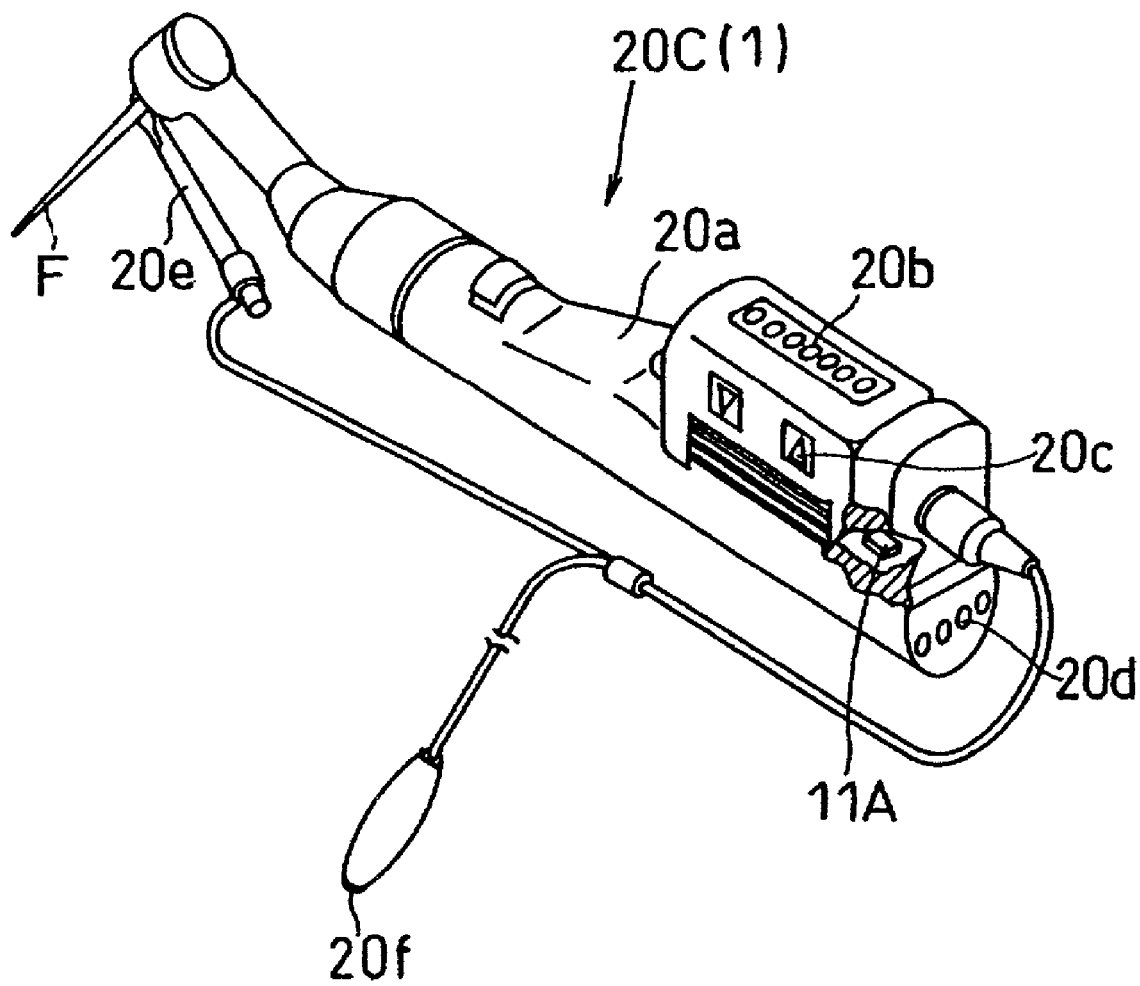

FIG. 15 is an external perspective view of other embodiment of a functional module according to the present invention.

Figure 16:
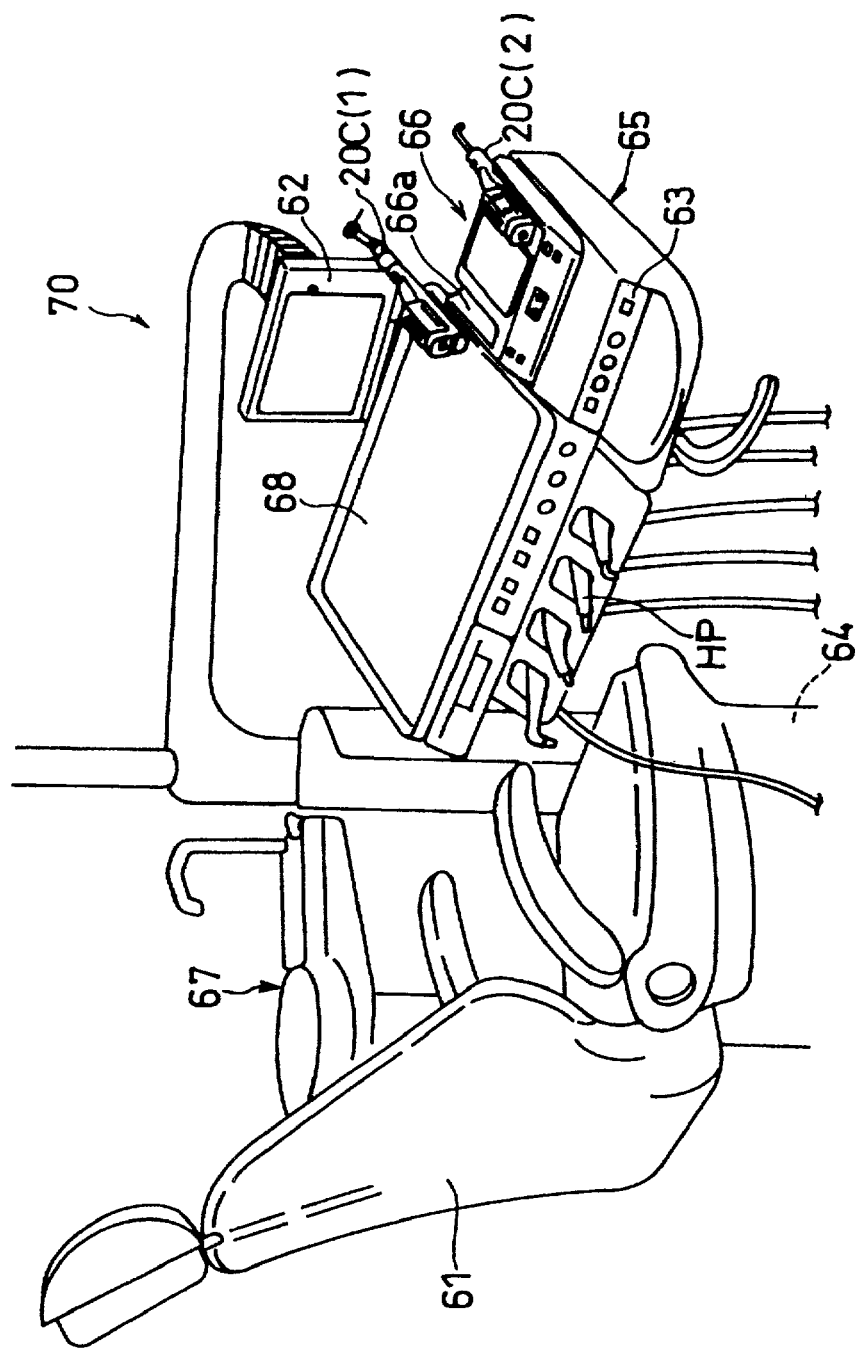

FIG. 16 is an external perspective view of one embodiment of the medical treatment and/or diagnosis apparatus using the functional module.

Figure 17:
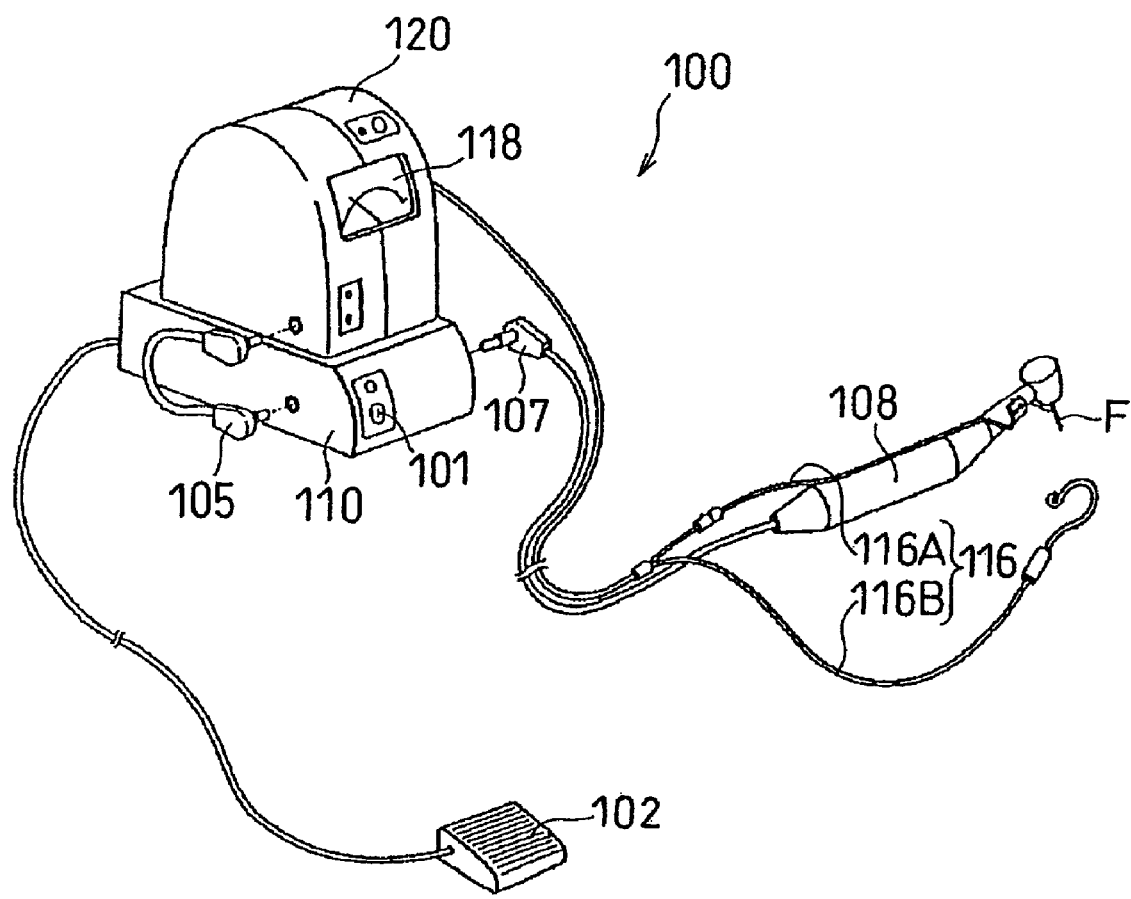

FIG. 17 is an external perspective view of a complex type medical treatment and/or diagnosis apparatus in the prior art.

DETAILED DESCRIPTION OF THE INVENTION

Embodiments of the present invention will be explained referring to the attached drawings. In this specification a functional module type medical apparatus for use in medical treatment and/or diagnosis, a functional module for the apparatus, a medical system for use in medical treatment and/or diagnosis using the functional module and a medical functional module unit for use in medical treatment and/or diagnosis are explained in case of dental application, however, the field of the present invention isn't limited in the field of dentistry.

FIG. 1 is one embodiment of a functional module type medical apparatus for use in medical treatment and/or diagnosis and a functional module according to the present invention, FIG. 1a is an external perspective view when both of them are combined, FIG. 1b is an external perspective view of the medical apparatus, and FIG. 1c is an external perspective view of the functional module.

FIG. 1a shows when a functional module 20 having a desired treatment and/or diagnosis function is incorporated to be combined with a functional module type medical apparatus 10 for use in medical treatment and/or diagnosis, only the medical apparatus 10 is shown in FIG. 1b, and only the functional module 20 is shown in FIG. 1c The medical apparatus 10 for use in medical treatment and/or diagnosis is provided with a display section 1 displaying necessary information for a treatment and/or diagnosis purpose, an operation section 2 for inputting for a treatment and/or diagnosis purpose, a common functional body 4 having a power source 3 for supplying a driving power of the apparatus 10, a module connection part 5 (will be detailed later) for replaceably connecting the functional module 20 having an individual treatment and/or diagnosis function.

The common functional body 4 isn't limited to one having all of the display section 1, the operation section 2 and the power source 3, and it may have any one of them or may be provided with other common functions solely or in combination.

In this embodiment, a root canal length measuring function is further provided for the medical apparatus 10 as a treatment and/or diagnosis function. In such a manner, the apparatus 10 may have a treatment and/or diagnosis function which is usually provided for the functional module and may execute a certain treatment and/or diagnosis by itself. In addition, an individual treatment and/or diagnosis function in this specification includes not only a simple function such as measuring a root canal length, enlarging a root canal and so on but also a combined function which can achieve those plural functions.

The functional module 20 has an individual treatment and/or diagnosis function, a connection part 12 for replaceably connecting to the medical apparatus 10, and a recognition apply means for the purpose of self-recognition of the medical apparatus 10 (not shown and will be explained later). This functional module is provided with a root canal enlarging function in this embodiment. However, an individual treatment and/or diagnosis function includes a combined function other than such a simple function.

The medical apparatus 10 for use in medical treatment and/or diagnosis is provided with a root canal length measuring function so as to be able to measure a root canal length by itself. However, the common functional body 4 can be also used for enlarging a root canal other than measuring a root canal. The functional module 20 with a root canal enlarging function is designed to be incorporated with the module connection part 5 as shown in FIG. 1a so that both of them are electrically and mechanically connected so as to enlarge a root canal while measuring a root canal length as a whole system. Further, the parts other than a root canal are prevented from being enlarged by mistake.

Such a characteristic is common with that of a conventional medical apparatus 100 shown in FIG. 17. However, the medical apparatus 10 for use in medical treatment and/or diagnosis of the present invention may be replaceably attached with the functional module 20 which has not only a root canal enlarging function as mentioned above but also other functions required for dental treatment such as having a function of a micromotor handpiece, a scaler, a photo polymerization device, a semiconductor laser, a root canal enlarging device, and a root canal charging device, all of which are used for treatment; and a function of a dental caries detector, a root canal length measuring device, a pulp tester, an intraoral camera, and a pocket measuring device.

According to this medical apparatus 10 for use in medical treatment and/or diagnosis, it has been found that there is a common functional part which is always used commonly and an individual functional part which is specified corresponding to each treatment and/or diagnosis purpose. When those individual functional parts are designed to be exchangeable as a functional module, the common functional parts are prevented from being overlapped, thus cutting out expenditure. Thereby, the cost of each individual functional part is reduced.

In other words, if plural treatment and/or diagnosis functions are required for a treatment purpose, the medical apparatus of the present invention can save a space for apparatus, reduce the cost and be made compact irrespective of the types of treatment and/or diagnosis functions.

The functional module which is used combining with such a functional module type medical apparatus for use in medical treatment and/or diagnosis is also required to correspond to the medical apparatus. The module can achieve the same effect as the functional type medical apparatus when they are combined to be cooperated.

According to the combination of the functional module type medical apparatus for use in medical treatment and/or diagnosis and the functional module, each one is comprehended as one unit. However, the combination can be comprehended as a medical apparatus 30 as a whole.

Further, the entire body may be comprehended as a medical functional module unit 40 and each body is comprehended as a functional module comprising the medical functional module unit 40, for example, a common functional module unit 34 having a display section 31, an operation section 32 and an energy supply means 33 including an electric power and an individual functional module unit 36 which is comprised by incorporating a required drive controller (not shown) corresponding to an individual treatment and/or diagnosis function.

In such a case, plural types of individual functional module unit 36 are replaceably attached to the common functional module unit 34 so as to be used together. The connection between the common functional module unit 34 and each individual functional module unit 36 is understood as a common electrical connection portion 37 and a common mechanical connection portion 38 for connecting the units 34 and 36 to be incorporated.

In either case of such a medical apparatus 30 for use in medical treatment and/or diagnosis and such a medical functional module unit 40, it can achieve the same effect as the above-mentioned medical apparatus 10 for use in medical treatment and/or diagnosis and the functional module 20 although only the comprehension methods of each construction are different.

Figure 2A:
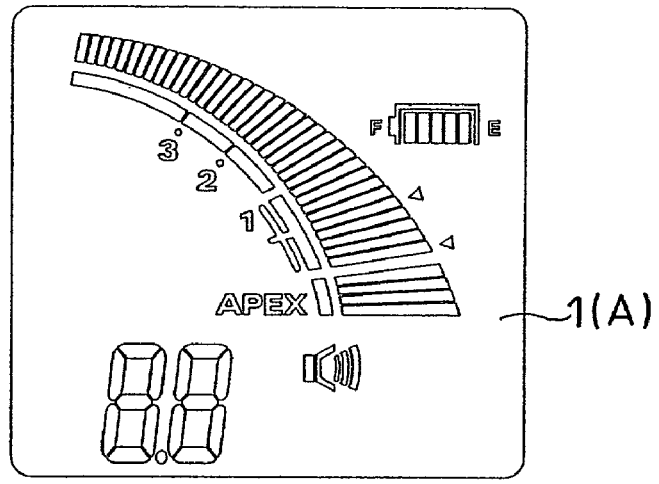
FIG. 2*a* shows a sample view when a root canal length is measured.
Figure 2B:
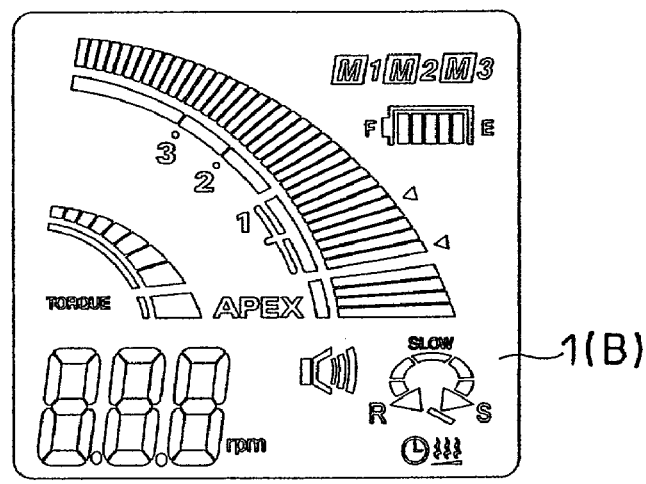
FIG. 2*b* is a sample view when a root canal length is measured and a root canal is enlarged.
Figure 2C:
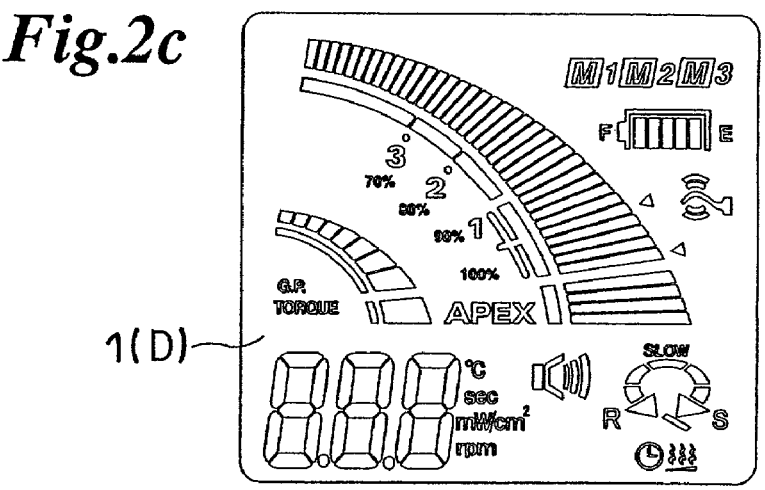
FIG. 2*c* is a sample view when all items are appeared.

FIG. 2 is display section samples according to the present invention, FIG. 2a shows a display section when a root canal length is measured, FIG. 2b is a display section when a root canal length is measured and a root canal is enlarged, FIG. 2c is a display section when all items are shown. Referring to the drawings, samples of a display section which functions as a common functional body will be explained. The members which have been already explained have the same numerals and their explanations are omitted hereinafter.

In these figures, the display section 1(A) shows when a root canal length is measured, the display section 1(B) shows when a root canal length is measured and a root canal is enlarged, and the display section 1(D) shows all items which can be shown on the display section 1 for the purpose of explanation.

On the display section 1(D), display items required for a photo polymerization device, a scaler, and a root charging device are shown other than display items required for measuring root canal length and enlarging a root canal.

In this sample, the display section 1 can show all kinds of information in a combination of plural display items supposing information required for several kinds of treatment and/or diagnosis functions in advance so as to selectively display information depending on treatment and/or diagnosis functions. According to such a display section, a screen is visible from an oblique position.

On the other hand, a general-purpose CRT or a liquid crystal screen may be used as a display section and in such a case the flexibility of the display section becomes wide because display data are merely required to be prepared.

FIG. 3 shows several types of operation section corresponding to the display sections of the present invention, FIG. 3a1 FIG. 3a2 and FIG. 3a3 are a button type, a button type with a display section, a display section integrated type respectively when the display section shows when a root canal length is measured. FIG. 3b1, FIG. 3b2 and FIG. 3b3 show each same panel when a root canal length is measured and a root canal is enlarged.

Display means and input means have been able to be combined to work together, such as a touch panel, according to the progress of information processing technology in recent years. This specification shows some samples of the combinations of a display section and an operation section corresponding to the technological progress.

The operation section 2 in FIG. 3a1 and FIG. 3b1 is a button type wherein operation contents are displayed on an operation display section 1a which is a part of the display section 1. When the treatment and/or diagnosis function is changed from measuring a root canal to measuring a root canal and enlarging a root canal by adding functional modules as shown in this embodiment, the display section 1a is changed corresponding to the functions and also the functions of the three buttons 2a are changed.

The control panel 2A of FIG. 3a2 and FIG. 3b2 is a button type with a display section in such a manner that each button 2b can display its function by means of characters.

The control panel 2B of FIG. 3a3 and FIG. 3b3 is a display section integrated type combined with the display section 1, namely a touch panel type.

FIG. 4 is a block diagram showing one embodiment of a medical apparatus for use in medical treatment and/or diagnosis and a functional module according to the present invention.

The medical apparatus 10 for use in medical treatment and/or diagnosis is provided with the display section 1, the control panel 2, the power source 3, the common functional body 4, and the module connection part 5, which have been already explained. The apparatus 10 further has a module recognition means 6 (will be detailed hereinafter) for discriminating which functional module 20 is connected, a multi-joint type connection part (connector) 7, a multi-joint type instrument 8 capable of detachably connecting to the multi-joint type connection part 7, a central processing unit 9a controlling the entire medical apparatus 10, and a root canal measuring circuit 9b exerting a root canal measuring function.

The power source 3 has a battery 3a consisting a drive power and a switch 3b for switching on-off connection to the battery 3a. In the figure an electrical connection portion 5a of the module connection part 5 is shown.

As explained in FIG. 1, the medical apparatus 10 for use in medical treatment and/or diagnosis is provided with the canal root length measuring circuit 9b so as to be able to measure a canal root length by itself. For this purpose, the connected instrument 8 is for measuring a canal root length and is provided with a positive electrode 8a and a negative electrode 8b.

The instrument 8 and the connector 7 are multi-joint type so that several kinds of instruments other than one measuring device can be replaceably and detachably connected. After being connected, identification signals are sent to the medical apparatus 10 from the instrument 8 and the apparatus 10 recognizes which instrument is connected by means of the signals, thereby achieving the function depending on the connected instrument.

Such a multi-joint type instrument has been detailed in JP-A-2000-254153 and JP-A-2000-288001 filed by the applicant of the present invention.

The functional module 20, in addition to the connection part 12 as mentioned above, is provided with recognition apply means 11 for the purpose of self-recognition of the medical apparatus 10, a power source 13 having a battery 13a and a switch 13b for switching the connection to the battery 13a, a multi-joint type connection portion 15, an instrument 16 capable of detachably connecting the connection part 15, a central processing unit 18a for entirely controlling the functional module 20, a motor drive circuit 18b for drive-controlling a motor for enlarging a root canal and an operation section 18c for inputting required data.

In the figure, an electrical connection portion 12a of the connection 12 is shown.

The instrument 16 in this embodiment is a motor handpiece for measuring a root canal length and enlarging a root canal. It is multi-joint type and has a handpiece 16a, a motor 16b for rotary driving a file F, and a positive electrode 16c and a negative electrode 16d for measuring a root canal length.

The functional module type medical apparatus 10 and the functional module 20 are thus combined, resulting in achieving the above-mentioned effects.

The medical apparatus 10 and the functional module 20 are entirely driven by means of the switch 3b and 13b provided for the power source 3 and 13 respectively, namely by the battery 13a provided for the functional module 20 in such a manner that the battery 3a of the medical apparatus 10 isn't used or is removed when the functional module 20 is connected.

FIG. 5a is a flow chart explaining one embodiment of operational procedures of a medical apparatus for use in medical treatment and/or diagnosis and a functional module according to the present invention and FIG. 5b shows a memory map of a medical apparatus.

Referring to FIG. 4 and FIG. 5, operational procedures for executing an individual treatment and/or diagnosis function by connecting and combining the medical apparatus for use in medical treatment and/or diagnosis and the functional module will be explained.

When the medical apparatus 10 and the functional module 20 are connected as shown in FIG. 1a, the mechanical connection therebetween and the connection between the electrical connection portions 5a and 12a as shown in FIG. 4 are also achieved.

Under such a condition, when the medical apparatus 10 is started to be operated, the functional module 20 is simultaneously started so that a request for transmitting a module code is executed from the medical apparatus 10. Upon receiving the request, the functional module 20 transmits a module code by the recognition apply means 11, then the medical apparatus 10 recognizes which functional module 20 is connected by a module recognition means 6 upon receiving module code signals (S1, S2) to be a standby mode for receiving the functional programs.

Then, when the functional module 20 transmits the functional program (control software) storing therein to the medical apparatus 10 (S12), the apparatus 10 receives the program (S2) to store it in a location after 4000H in the memory map as shown in FIG. 5b.

After receipt, the medical apparatus 10 transfers its process to a location (4000H) where the stored functional program exists (S3), sets the display section 1 and the operation section 2 into a mode corresponding to the treatment and/or diagnosis function of the connected functional module 20 and while sending and receiving data with the functional module 20 if required (S13), the functional program of the functional module 20 is executed (S4).

Communication is thus executed between the medical apparatus 10 for use in medical treatment and/or diagnosis and the functional module 20 so that the medical apparatus 10 can use the treatment and/or diagnosis function of the connected functional module 20 by sending and receiving several kinds of data therebetween. In such a manner, if the version of a control software for treatment and/or diagnosis function is upgraded, necessary correspondence can be done by exchanging a control software memory means (ROM) of the functional module or exchanging for a new functional module.

The "module code" used in this specification is an idea including several types of signals and codes for recognizing the functional module. For example, a code "100010" may be used for the functional module providing a root canal measuring function or a code "010101" may be used for the functional module having a photo polymerization function.

The communication information between the medical apparatus 10 for use in medical treatment and/or diagnosis and the functional module 20 is preferably at least any one of a display regarding the treatment and/or diagnosis function of the functional module 20, an operational input, information on medical treatment and/or diagnosis data, and the instrument machinery or control information about the connected instruments 8 and 16.

FIG. 6 is a flow chart explaining other embodiment of operational procedures of a medical apparatus for use in medical treatment and/or diagnosis and a functional module according to the present invention.

In this embodiment the connected medical apparatus for use in medical treatment and/or diagnosis and the functional module are separately operated in such a manner that common universalized signals required for each control are sent and received therebetween so that a required treatment and/or diagnosis function is achieved as a whole.

For this purpose, a general-purpose software capable of corresponding to supposed several types of treatment and/or diagnosis function is stored in the medical apparatus 10.

In this case when the medical apparatus 10 is operated to start, the functional module 20 is also operated to send a module code therefrom. Upon receiving the module code, the medical apparatus 10 recognizes which functional module 20 is connected as shown in the flow chart in FIG. 5 (S21, S31).

Then, the medical apparatus 10 reads out a control software corresponding to the recognized treatment and/or diagnosis function from the general-purpose software, not that an individual functional program (control software) is sent from the functional module 20. Accordingly, the display section 1 and the operation section 2 are set in a mode corresponding to the read out treatment and/or diagnosis function so as to achieve the treatment and/or diagnosis function.

In the meantime, the medical apparatus 10 and the functional module 20 respectively execute its self unique process corresponding to the treatment and/or diagnosis function, for example the apparatus 10 measures a root canal length and the function module 20 enlarges a root canal (S23, S32). They send and receive universalized signals if required to request display and data correction or corresponding treatment for these requests are executed (S24, S33).

Also in such a manner the medical apparatus 10 for use in medical treatment and/or diagnosis and the functional module 20 are communicated so that the apparatus 10 can use the treatment and/or diagnosis function of the connected functional module 20 by sending and receiving several data therebetween.

If the functional module 20 has any functions, one of the combinations of the display element as shown in FIG. 2 is selected and on-off signals are sent for operating the operation section 2, so that processes thereafter can be left for the functional module 20.

If the communicated signals are universalized signals, the operation of the medical apparatus 10 can be kept within a fixed range even if any functional module is connected.

Samples of the universalized signals are a request signal to send module code, a request signal to resend, a request signal to display and draw on the display, a request signal to revise data, a request signal to upgrade a control software, a signal to send operational condition of the operation section, and so on.

The control software stored in the above-mentioned functional module and the general-purpose control software stored in the medical apparatus may be forwarded by providing a communication line for these apparatus, enabling easy upgrade of the software.

FIG. 7 explains a connection between a medical apparatus for use in medical treatment and/or diagnosis and a functional module according to the present invention, FIG. 7a explains a combining method of the apparatus and the module, FIG. 7b is a sectional view of a substantial part of the connection part, and FIG. 7c is a sectional view of a substantial part of an electrical connection portion.

Mechanical association means 5b and 12b and engaging members 5c and 12c for defining positional engagement between both connections 5 and 12 are provided for the module connection part 5 of the medical apparatus 10 and the connection part 12 of the functional module 20, as shown in the figures, in addition to the mechanical connection portions 5a and 12a as already explained.

The medical apparatus 10 with the connection part 5 and the functional module 20 having the connection part 12 are engaged as shown by the arrow lines in FIG. 7a in such a manner that the connection parts 5c and 12c are engaged at first to fit the association means 5b and 12b. The association means 5b energized into right in FIG. 7c is once pushed by the association means 12b to be returned into left and finally the apparatus 10 and the module 20 are engaged as shown in FIG. 7b and FIG. 7c, achieving connection of the electrical connection portions 5a and 12a.

For separating, the association means 5b of the medical apparatus 10 is moved left in FIG. 7b and FIG. 7c by manual operation to remove fitting of the association means 5b and 12b, resulting in removal of the functional module 20.

In such a manner the medical apparatus 10 for use in medical treatment and/or diagnosis and the functional module 20 can be easily and replaceably detached. Once engaged, they are mechanically and functionally incorporated so as to achieve desired treatment and/or diagnosis functions cooperatively.

Further the electrical connection and the mechanical connection can be simultaneously accomplished, however, the electrical connection may be executed by connection wires like prior arts.

If the parts relating to the connection, for example the electrical connection portions 5a, 12a, the association means 5b, 12b and the engaging parts 5c, 12c are made common or standardized, any functional modules are able to be connected with any medical apparatus for use in medical treatment and/or diagnosis.

FIG. 8 is an external perspective view of a medical apparatus for use in medical treatment and/or diagnosis, a functional module and a multi-joint type instrument according to the present invention.

In the figure, the reference numeral 18d shows a substrate incorporated in the functional module 20 and mounting electrical members such as recognition apply means 11. Connection terminals are lined on the electrical connection portion 12a of the connection parts 12. When the medical apparatus 10 and the functional module 20 are connected, these connection terminals and the connection terminals of the medical apparatus are electrically connected.

The instrument 16 is multi-joint type as mentioned above and a connection code 16e itself is multi-joint type in this embodiment. Further, the connection between the connection code 16e and the connection 15 of the functional module 20 and the connection between the connection code 16e and a handpiece 16a are also multi-joint type. Therefore, different types of connection code 16e can be replaceably connected to the connection 15 of the functional module 20 or different types of handpiece 16a with various torques and maximum revolution speeds can be replaceably attached to the connection code 16e.

Furthermore, the recognition apply means 11A using ID elements is incorporated in each connection code 16e and the handpiece 16a so that the medical apparatus 10 for use in medical treatment and/or diagnosis in addition to the functional module 20 can receive ID codes for controlling individual control data such as its manufacturing date and its serial number other than the types of connected code 16e and connected handpiece 16a.

Module recognition means will be explained referring to FIG. 9, FIG. 10 and FIG. 11.

The module recognition means explained here is not for the apparatus 10 recognizing the connected functional module 20 but for the functional module 20 recognizing the connected instrument. However, the same construction may be used between the medical apparatus 10 and the functional module 20. Such a case is shown as a modified embodiment of the module recognition means.

FIG. 9a is a conceptual view showing one embodiment of a connector constructing a module recognition means of a medical apparatus for use in medical treatment and/or diagnosis according to the present invention, FIG. 9b shows a conceptual view of one embodiment of an individual connector of the functional module to be used incorporating into the connector in FIG. 9a, and FIG. 9c is a conceptual view showing another embodiment of an individual connector. FIG. 10 explains a recognition method for a functional module by the module recognition means.

The module recognition means shown in FIG. 9 and FIG. 10 is for mechanically and electrically detecting the shape of the individual connector of the instrument.

For this purpose individual connectors 16f(1) and 16f(2) constructing each connection of the instruments 16(1) and 16(2) have recognition projections LT, different numbers of the projections being provided at different places depending on the kinds of instruments, and have an engaging cut-out for regulating a rotary position for connecting with others.

The connector 15A of the functional module has electrical terminals P, plural limit switches LSA, LSB, LSC and LSD, and an engaging cut-out C so as to align the position of the recognition projection LT of the individual connector 16.

The functional module 20 incorporates a limit switch detection circuit 18e to receive detection signals from these limit switches LSA, LSB, LSC and LSD and an electrode switch circuit 18f for switching connection into an electrode P upon receiving output from the limit switch detection circuit 18e.

When the instrument 16(1) is connected to the connection 15A so as to meet both cut-outs C, only the limit switch LSA is turned on, thereby recognizing the instrument 16(1). The connection of the electrode P is accordingly switched. When the instrument 16(2) is connected, the limit switches LSA and LSC are turned on to recognize the instrument 16(2), and the electrode P is correspondingly switched.

FIG. 11 is a conceptual view showing other embodiment of module recognition means of a medical apparatus for use in medical treatment and/or diagnosis according to the present invention.

According to this module recognition means, different impedances I(1)-I(4) are incorporated in an individual instrument 16A(1)-16A(4). The impedances I(1)-I(4) of the instruments 16A(1)-16A(4) connected to the connector 15B are detected by an impedance detection circuit 18g incorporated in the functional module 20 so as to detect which one of the instruments 16A(1)-16A(4) is connected, thereby sending a switch command to an electrode switch circuit 18f.

In FIG. 9, FIG. 10 and FIG. 11, the module recognition means between the connection of the functional module and the instrument to be connected therewith is explained, however, the same construction may be used for the connection between the medical apparatus 10 for use in medical treatment and/or diagnosis and the functional module 20 as mentioned above.

FIG. 12 is an external perspective view showing other embodiment of a functional module type medical apparatus for use in medical treatment and/or diagnosis and a functional module according to the present invention.

In this embodiment, plural connections 5A, 4 connections in this embodiment, are provided for a functional module type medical apparatus 10A for use in medical treatment and/or diagnosis and a functional module 20A having a connection 12A corresponding to each connection 5A is designed to be replaceably connected to any one of the connection parts 5A.

In such a manner, plural numbers of functional modules 20A having an individual treatment and/or diagnosis function can be connected to the medical apparatus 10A for use in medical treatment and/or diagnosis as the need arises, resulting in various treatment and/or diagnosis function.

FIG. 13 is an external perspective view showing still other embodiment of a functional module type apparatus for use in medical treatment and/or diagnosis and a functional module according to the present invention.

In this embodiment, the functional module type medical apparatus 10 for use in medical treatment and/or diagnosis is the same as mentioned above, however, this embodiment is characterized in that the functional module 20B to be connected is provided with a sub module connection part 19 for replaceably connecting with other functional module in addition with the connection parts 12 to the medical apparatus 10.

Therefore, different functional modules 20B having an individual treatment and/or diagnosis function can be multiply connected as shown in the figure and various treatment and/or diagnosis functions can be achieved by one medical apparatus 10 like FIG. 12.

FIG. 14 is an external perspective view showing still other embodiment of a functional module type medical apparatus for use in medical treatment and/or diagnosis and a functional module according to the present invention, FIG. 14a shows when they are combined, and FIG. 14b shows when each module is separated.

In this embodiment, the characteristic of the present invention, namely functional modularization, is gone further.

In other words, while keeping an idea of common functional part, the common functional part is further modularized to be a display module 51, an operation module 52, and a power source module 53. Those modules are replaceably and detachably combined with plural functional modules 54(1) and 54(2) having an individual treatment and/or diagnosis function each other to accomplish required treatment and/or diagnosis function as a whole.

Each module 51-54 has a standardized connection so as to be able to select only a required module to be combined according to need.

The functional modules 54(1) and 54(2) may have a simple display section 54a and a simple operation section 54b if required. In such a case if the functional module 54(1) having the operation section 54b is combined with the power source 53 or the functional module 54(2) having the display section 54a and the operation section 54b is combined with the power source 53, a predetermined treatment and/or diagnosis function can be accomplished.

FIG. 15 is an external perspective view of other embodiment of a functional module according to the present invention and FIG. 16 is an external perspective view of one embodiment of a medical system for use in medical treatment and/or diagnosis using the functional module.

The functional module 20C shown in these figures incorporates a power source having a rechargeable battery (not shown) and is designed to achieve a desired treatment and/or diagnosis function by sending and receiving required data via wireless communication with a connected partner.

The functional module 20c(1) is for example provided with a motor handpiece 20a comprising a main body with a wireless function, a display section 20b provided for the handpiece 20a, an operation section 20c and a terminal 20d for recharging the battery, resulting in enlarging a root canal by attaching a file F at the tip of the handpiece 20a.

Further the functional module 2C(1) has a positive electrode 20e and a negative electrode 20f for achieving a root canal length measuring function. Furthermore, the module 20C(1) is provided with a recognition apply means 11A comprised of ID elements like the one incorporated in the multi-joint type instrument 16 shown in FIG. 8 so that the ID code from the recognition apply means 11A is wirelessly sent as a module code.

Such a functional module 20C is combined with a medical system 70 shown in FIG. 16 to be used together.

The medical system 70 includes a treatment table 61 for keeping a patient sitting or lying supine, a display section 62 for showing required information for treatment and/or diagnosis, an operation section 63 for receiving operation input for treatment and/or diagnosis, a common functional body 65, such as a power source 64 for supplying operational electricity for treatment and/or diagnosis incorporated in the treatment table 61, a module connection part 66 used as a table for the functional module 20C, a spittoon 67 for a patient rinsing out, and a movable table 68 for mounting equipment required for treatment and/or diagnosis and the above-mentioned module connection part 66.

Several kinds of handpieces HP are contained in the table 68 so as to take in and out.

The module connection part 66 contains a wireless communication function with the functional module 20C and is provided with a receiving recess 66a having terminals corresponding to the terminals 20b of the functional module 20C so as to replaceably hold the functional module 20.

In this case, only the functional module 20C is held and the rechargeable battery contained in the functional module 20C can be recharged via the terminal 20b. However, an individual treatment and/or diagnosis function of each functional module 20C is achieved by wirelessly sending and receiving required data with the module connection part 66. Such a wireless connection is included in the field of the present invention wherein a medical system or apparatus is replaceably connected with a functional module.

FIG. 16 shows two types of functional module 20C(1) and 20C(2) used for the medical system 70. The module 20C(1) has a root canal length measuring function and a root canal enlarging function like the one shown in FIG. 16 and the module 20C(2) has a photo polymerization function.

If a Bluetooth is used for wireless communication between the medical system 70 and the functional module 20C, inexpensive and point to point connection, and further point to multipoint connection are enabled.

The invention claimed is:

1. A functional module type dental apparatus for use in dental treatment and diagnosis, comprising:
   a common functional body and a functional module detachably and replaceably connected to said common functional body, and wherein
   the common functional body has a display section for displaying information relating to dental treatment and diagnosis, an operation section for dental treatment and diagnosis, a power source section for supplying driving power thereto, a module connection part to which said functional module is detachably and replaceably connected, a module recognition means for discriminating which functional module is connected when said functional module is connected to said module connection part, and a root canal length measuring function as at least one dental diagnosis function so as to carry out said root canal length measuring function,
   said functional module has a connection part for detachably and replaceably connecting to said module connection part of said common functional body, a recognition apply means for allowing said module recognition means to recognize itself, a dental treatment function, and a memory means storing a functional program for executing the dental treatment function, and said functional program is transmitted to said common functional body from said functional module after said module recognition means discriminates said functional module, thereby changing said display section and said operation section to a necessary display mode and a necessary operational function, respectively, depending on the dental treatment function equipped with said functional module, and carrying out said dental treatment function of said functional module by utilizing said common functional body.

2. The functional module type dental apparatus as set forth in claim 1, wherein said module connection part is constructed such that said functional module is detachably connected thereto in an electrical or mechanical connection manner.

3. The functional module type dental apparatus as set forth in claim 2, wherein said module connection part is constructed such that said common functional body and said functional module are mechanically and functionally integrated when said functional module is connected to said module connection part.

4. The functional module type dental apparatus as set forth in claim 1, wherein said module recognition means discriminates which functional module is connected, by a module code which is stored in said functional module, when said module code is received from said functional module through mutual communication with said functional module.

5. The functional module type dental apparatus as set forth in claim 1, wherein said module recognition means discriminates an ID code sent from an ID element which is provided in said functional module, when said functional module is connected to said module connection part of said common functional body.

6. The functional module type dental apparatus as set forth in claim 1, wherein said module recognition means discriminates which functional module is connected, by detecting an intrinsic impedance of said functional module, when said functional module is connected to said connection part of said common functional body.

7. The functional module type dental apparatus as set forth in claim 1, wherein said module recognition means discriminates which functional module is connected, by detecting the shape of individual connector provided in said functional module, when said functional module is connected to said module connection part of said common functional body.

8. The functional module type dental apparatus as set forth in claim 1, wherein said common functional body and said functional module transmit and receive at least one of information about treatment data relating to said dental treatment function of said functional module, and machinery or control information about an instrument to be connected thereto.

9. The functional module type dental apparatus as set forth in claim 1, wherein said module connection part is constructed such that plural numbers of said functional module are connected thereto.

10. The functional module type dental apparatus as set forth in claim 1, wherein said common functional body further comprises a multi-joint type connection part to which various multi-joint type instruments are replaceably connected in correspondence with the function of said functional module.

11. The functional module type dental apparatus as set forth in claim 1, wherein said common functional body has a battery therein as a driving power source.

12. A dental functional module detachably and replaceably connected to said common functional body of said functional module type dental apparatus for use in dental treatment and diagnosis as set forth in claim 1, comprising a connection part for detachably and repleaceably connecting to said module connection part of said common functional body, a recognition apply means for allowing said module recognition means to recognize itself, a dental treatment function, and a memory means storing a functional program for executing the dental treatment function, wherein said functional program is transmitted to said common functional body after said module recognition means of said common functional body discriminates said functional module, thereby changing said display section and said operation section to a necessary display mode and a necessary operational function, respectively, depending on the dental treatment function equipped with said functional module, and executing said dental treatment function of said functional module by utilizing said common functional body.

13. The dental functional module as set forth in claim 12, wherein said connection part is so constructed as to be detachably connected to said common functional body in an electrical or mechanical connection manner.

14. The dental functional module as set forth in claim 13, wherein said module connection part is so constructed such that said common functional body and said functional module are mechanically and functionally integrated, when connected to said common functional body.

15. The dental functional module as set forth in claim 12, wherein said module connection part is made under the same standard for plural dental functional modules.

16. The dental functional module as set forth in claim 12, further comprising a multi-joint type connection portion to which various multi-joint type instruments are detachably connected.

17. The dental functional module as set forth in claim 1 or 13, wherein said functional module further comprises a sub module connection part to which dental functional module having individual function of dental treatment is replaceably connected.

18. The dental functional module as set forth in claim 12 or 13, wherein said functional module has a battery therein as a driving power source for executing dental treatment thereof.

19. A dental apparatus for use in dental treatment and diagnosis comprising a treatment bed for holding a patient in sitting position or lying in face up position, and a functional module type dental apparatus as set forth in claim 1.

20. The functional module type dental apparatus for use in dental treatment and diagnosis as set forth in any one of claims 1, 2 and 4 to 9, wherein said display section, said operation section and said power source section are made as a common module unit, each of which constitutes an unit construction body.

21. The functional module type dental apparatus as set forth in claim 20, wherein said common module unit has therein an energy supply means comprised of at least one of power supply circuit, water supply means and air supply means, each of supplies power, water or air to said functional module.

* * * * *